(12) United States Patent
Ladd et al.

(10) Patent No.: US 10,743,908 B2
(45) Date of Patent: Aug. 18, 2020

(54) TISSUE-REMOVING CATHETER INCLUDING DEPLOYMENT MECHANISM

(71) Applicant: Covidien LP, Mansfield, MA (US)

(72) Inventors: Bryan Ladd, Minneapolis, MN (US);
Lucas Schneider, Champlin, MN (US);
Daniel J. Vreeman, Ostego, MN (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 16/036,105

(22) Filed: Jul. 16, 2018

(65) Prior Publication Data
US 2018/0325546 A1 Nov. 15, 2018

Related U.S. Application Data

(63) Continuation of application No. 14/971,986, filed on Dec. 16, 2015, now Pat. No. 10,258,365, which is a
(Continued)

(51) Int. Cl.
*A61B 17/3207* (2006.01)
*A61B 17/00* (2006.01)
*A61B 17/32* (2006.01)

(52) U.S. Cl.
CPC ........... *A61B 17/320758* (2013.01); *A61B 17/320783* (2013.01); *A61B 2017/00292* (2013.01);
(Continued)

(58) Field of Classification Search
CPC ........ A61B 17/3207; A61B 17/320758; A61B 17/320783; A61B 2017/320741; A61B 2017/320766; A61B 2017/320775; A61B 2017/320791; A61B 2017/320024; A61B 2017/320028

See application file for complete search history.

(56) References Cited

U.S. PATENT DOCUMENTS 4,290,427 A 9/1981 Chin
4,631,052 A 12/1986 Kensey
(Continued)

FOREIGN PATENT DOCUMENTS

WO WO99/23958 5/1999
WO WO2012/064966 5/2012

OTHER PUBLICATIONS

Japanese Office Action in related application JP No. 2015-547406 dated May 30, 2016, 10 pages.
(Continued)

*Primary Examiner* — Melanie R Tyson

(57) ABSTRACT

A tissue-removing catheter includes a cutter having an axial cavity and an opening extending from the axial cavity through the cutter to allow tissue removed from the body lumen by the annular cutting edge to pass proximally through the opening toward a tissue-transport passage of a catheter body. A screw blade extends longitudinally within the interior passage of the catheter body includes an external helical thread for transporting removed tissue proximally within the tissue-transport passage as the screw blade rotates about its axis. A cutter driveshaft extends longitudinally within a driveshaft passage of the screw blade and is rotatable about its axis relative to the screw blade. The cutter driveshaft having a distal end portion operatively coupled to the cutter for driving rotation of the cutter.

20 Claims, 28 Drawing Sheets

Related U.S. Application Data continuation of application No. 14/101,875, filed on Dec. 10, 2013, now Pat. No. 9,241,734.

(60) Provisional application No. 61/736,169, filed on Dec. 12, 2012.

(52) U.S. Cl.
CPC .............. *A61B 2017/00685* (2013.01); *A61B 2017/320024* (2013.01); *A61B 2017/320741* (2013.01); *A61B 2017/320775* (2013.01); *A61B 2017/320791* (2013.01)

(56) References Cited

U.S. PATENT DOCUMENTS

| | | |
|---|---|---|
| 4,765,332 A | 8/1988 | Fischell et al. |
| 4,790,813 A | 12/1988 | Kensey |
| 4,862,518 A | 9/1989 | Williams et al. |
| 4,926,858 A | 5/1990 | Gifford, III et al. |
| 4,950,277 A | 8/1990 | Farr |
| 5,026,383 A | 6/1991 | Nobles |
| 5,078,722 A | 1/1992 | Stevens |
| 5,085,662 A | 2/1992 | Willard |
| 5,100,424 A | 3/1992 | Jang et al. |
| 5,123,904 A | 6/1992 | Shimomura et al. |
| 5,176,693 A | 1/1993 | Pannek, Jr. |
| 5,192,291 A | 3/1993 | Pannek, Jr. |
| 5,226,909 A | 7/1993 | Evans et al. |
| 5,242,460 A | 9/1993 | Klein et al. |
| 5,350,390 A | 9/1994 | Sher |
| 5,507,760 A | 4/1996 | Wynne et al. |
| 5,507,795 A | 4/1996 | Chiang et al. |
| 5,556,408 A | 9/1996 | Farhat |
| 5,569,277 A | 10/1996 | Evans et al. |
| 5,601,580 A | 2/1997 | Goldberg et al. |
| 5,620,456 A | 4/1997 | Sauer et al. |
| 5,762,069 A | 6/1998 | Kelleher et al. |
| 5,776,156 A | 7/1998 | Shikhman |
| 5,857,982 A | 1/1999 | Milliman et al. |
| 5,891,153 A | 4/1999 | Peterson |
| 6,053,923 A | 4/2000 | Veca et al. |
| 6,068,603 A | 5/2000 | Suziki |
| 6,110,127 A | 8/2000 | Suziki |
| 6,428,539 B1 | 8/2002 | Baxter et al. |
| 6,503,263 B2 | 1/2003 | Adams |
| RE38,018 E | 3/2003 | Anctil et al. |
| 6,579,298 B1 | 6/2003 | Bruneau et al. |
| RE38,335 E | 11/2003 | Aust et al. |
| 7,329,267 B2 | 2/2008 | Weber |
| 7,344,546 B2 | 3/2008 | Wulfmann et al. |
| 7,485,125 B2 | 2/2009 | Sjostrom |
| 7,520,886 B2 | 4/2009 | Surti |
| 7,635,340 B2 | 12/2009 | Vetter et al. |
| 7,699,790 B2 | 4/2010 | Simpson |
| 7,918,803 B2 | 4/2011 | Ritchart et al. |
| 7,927,784 B2 | 4/2011 | Simpson |
| 7,951,161 B2 | 5/2011 | Bonnette et al. |
| 7,981,128 B2 | 7/2011 | To et al. |
| 8,012,164 B1 | 9/2011 | Donohoe et al. |
| 8,052,704 B2 | 11/2011 | Olson |
| 8,062,316 B2 | 11/2011 | Patel et al. |
| 8,070,762 B2 | 12/2011 | Escudero et al. |
| 9,636,138 B2 | 5/2017 | Scheider |
| 2004/0006358 A1 | 1/2004 | Wulfman et al. |
| 2007/0055259 A1 | 3/2007 | Norton et al. |
| 2007/0276419 A1 | 11/2007 | Rosenthal |
| 2007/0282358 A1 | 12/2007 | Remiszewski et al. |
| 2008/0045986 A1 | 2/2008 | To et al. |
| 2008/0065124 A1 | 3/2008 | Olson |
| 2008/0140104 A1 | 6/2008 | Bender et al. |
| 2010/0198240 A1 | 8/2010 | Simpson et al. |
| 2011/0004107 A1 | 1/2011 | Rosenthal et al. |
| 2011/0087258 A1 | 4/2011 | Sluss |
| 2011/0130777 A1 | 6/2011 | Zhang et al. |
| 2011/0144673 A1 | 6/2011 | Zhang et al. |
| 2011/0152906 A1 | 6/2011 | Escudero et al. |
| 2011/0190801 A1 | 8/2011 | Mark et al. |
| 2011/0301626 A1 | 12/2011 | To et al. |
| 2011/0306995 A1 | 12/2011 | Moberg |
| 2012/0046679 A1 | 2/2012 | Patel et al. |

OTHER PUBLICATIONS

Japanese Office Action in related application JP No. 2015-547406 dated Feb. 6, 2017, 7 pages.

International Search Report and Written Opinion of related application PCT/US2013/072961 dated Apr. 7, 2014, 17 pages.

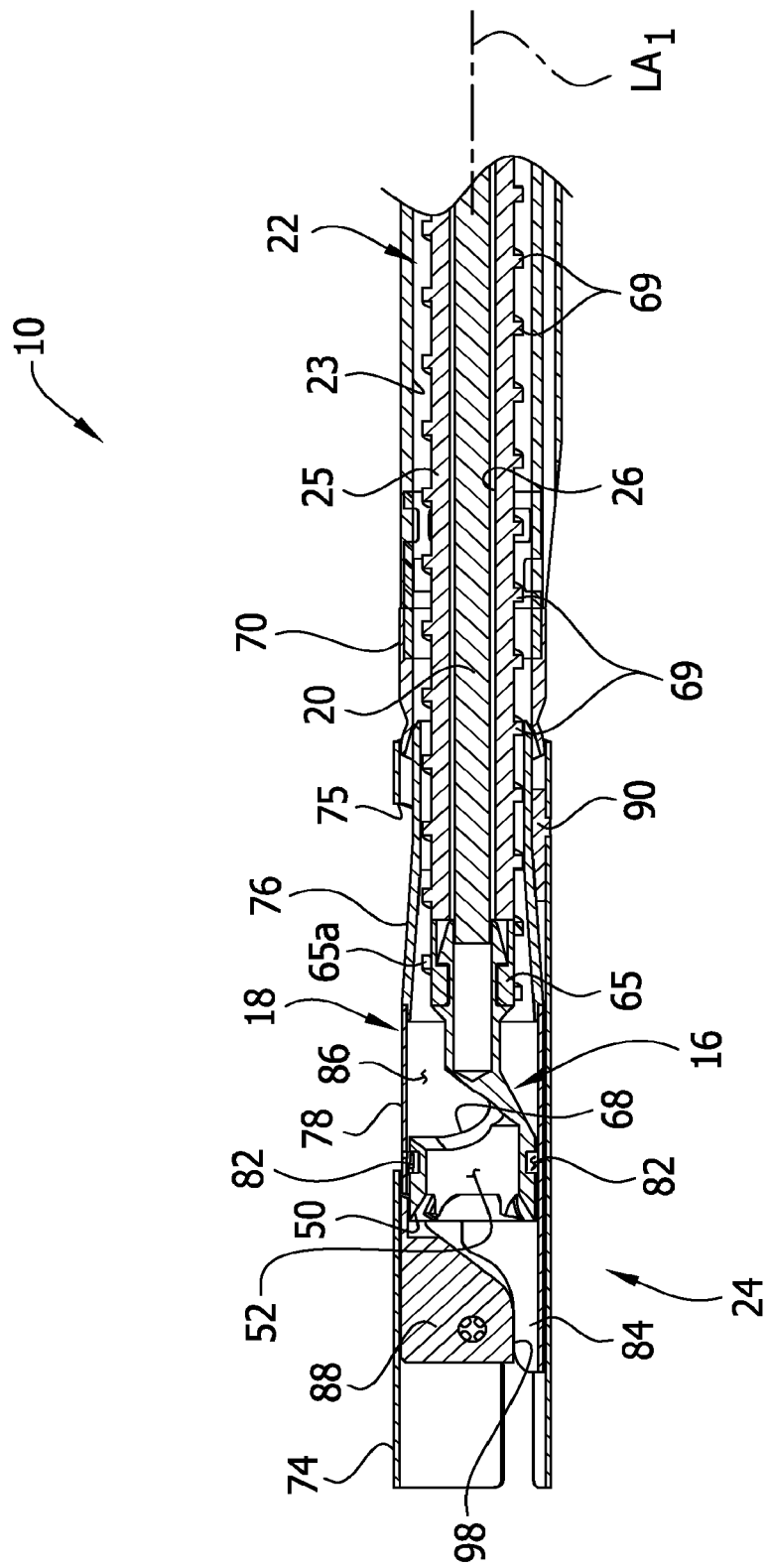

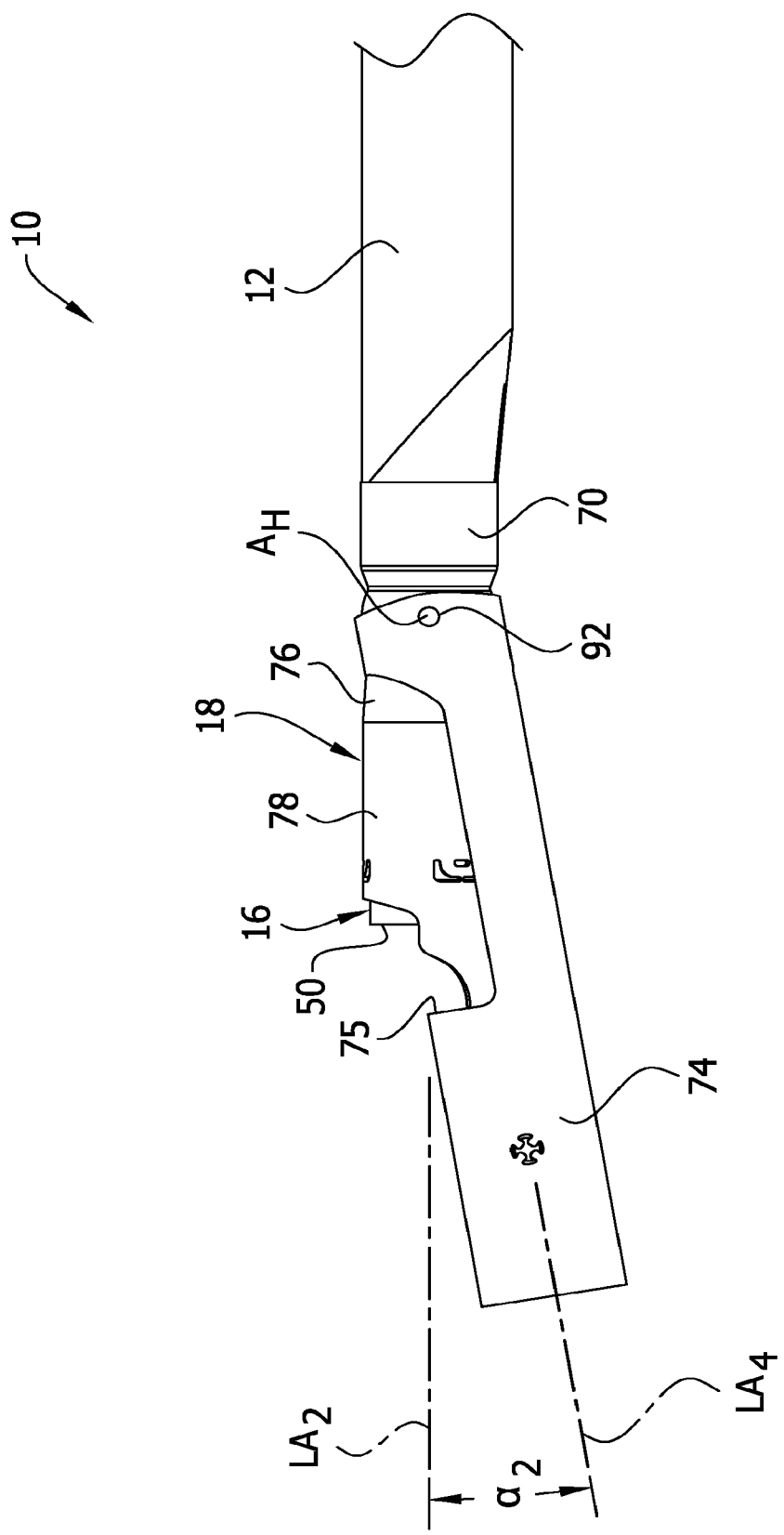

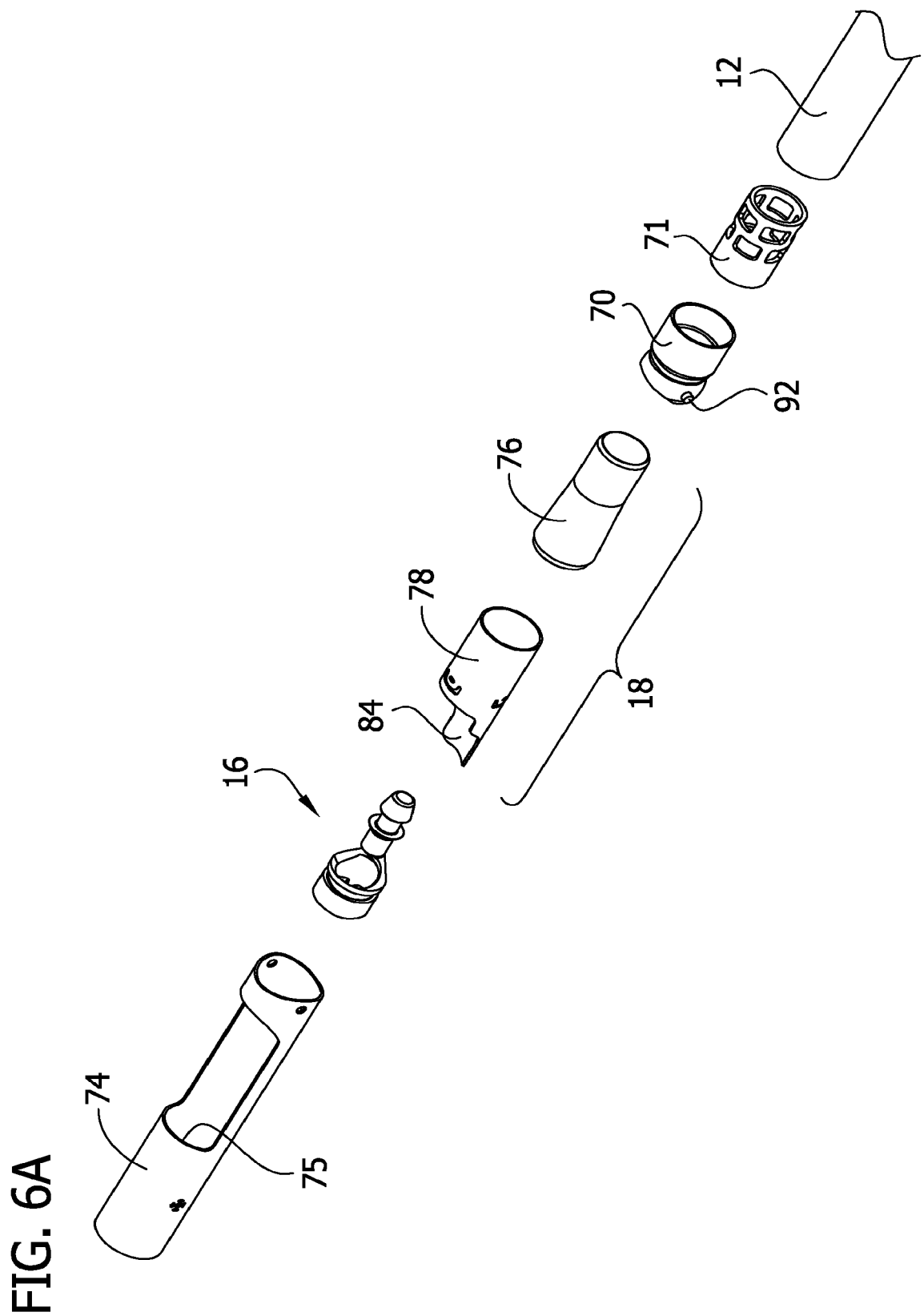

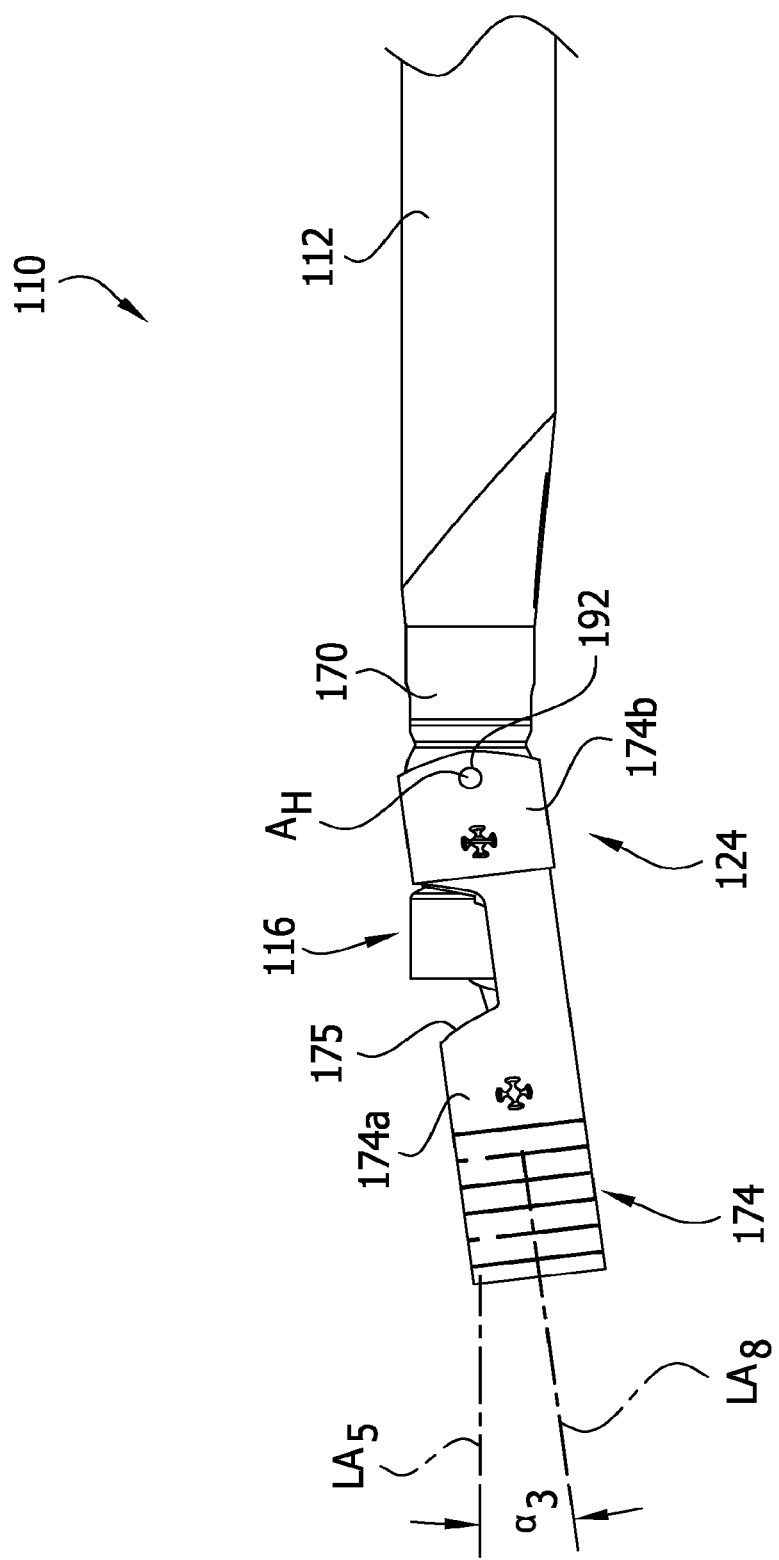

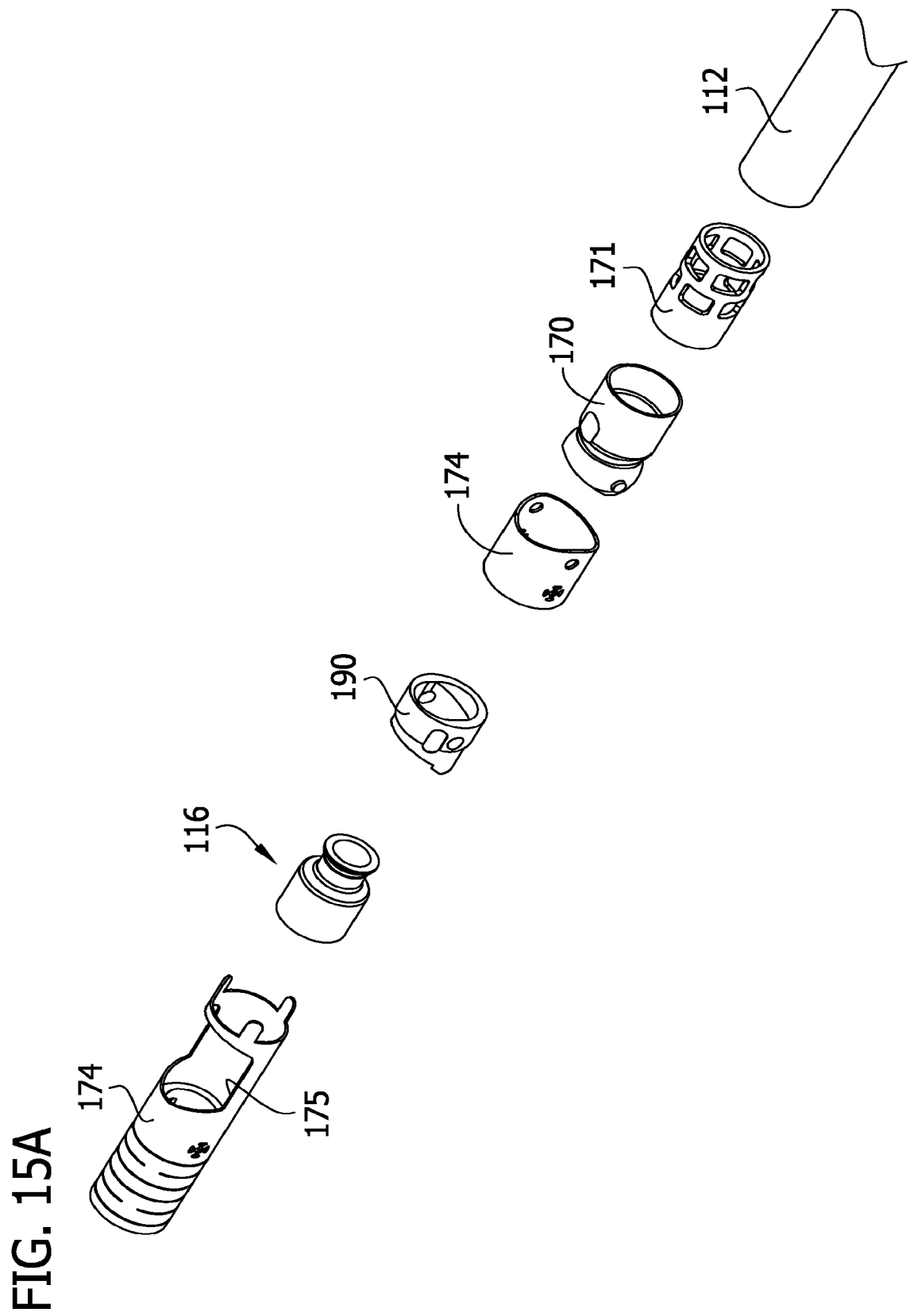

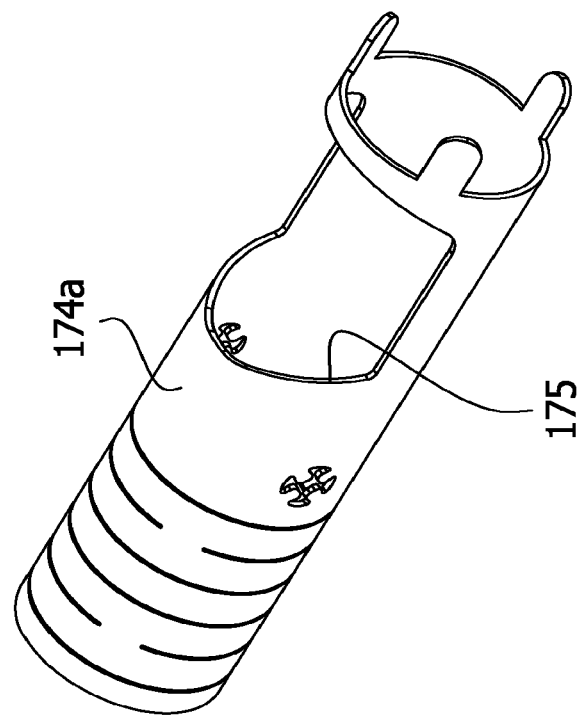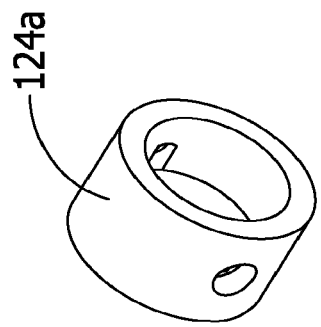
FIG. 15B

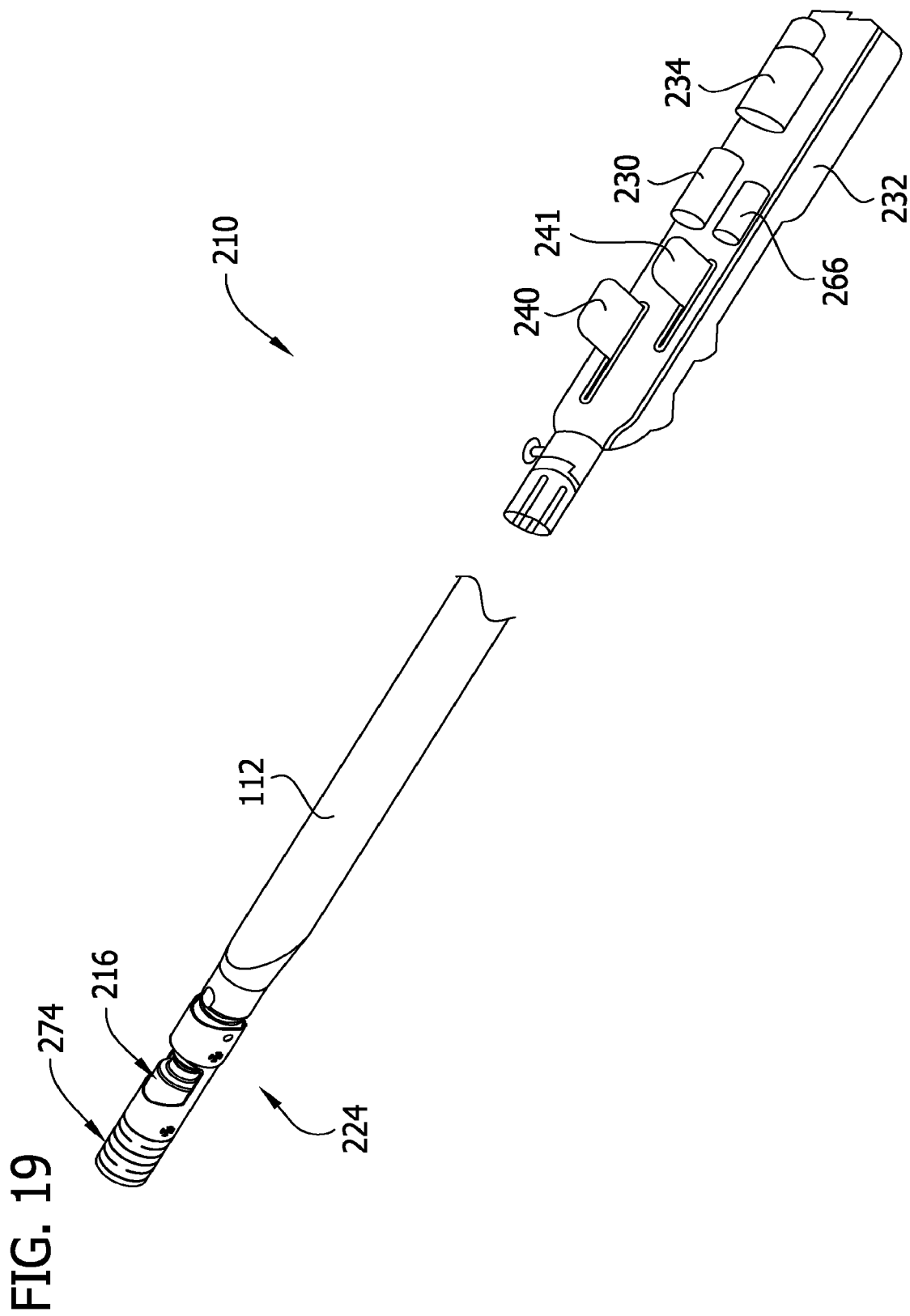

TISSUE-REMOVING CATHETER INCLUDING DEPLOYMENT MECHANISM

CROSS-REFERENCE TO RELATED APPLICATIONS

The present application is a continuation of U.S. Ser. No. 14/971,986, filed Dec. 16, 2015, issued as U.S. Pat. No. 10,022,143, which is a continuation of U.S. Ser. No. 14/101,875, filed Dec. 10, 2013, issued as U.S. Pat. No. 9,241,734, which claims priority to U.S. Provisional Application Ser. No. 61/736,169, filed Dec. 12, 2012, the entirety of each of which is hereby incorporated by reference.

FIELD OF THE DISCLOSURE

The present invention generally relates to a tissue-removing catheter for removing tissue from a body lumen.

BACKGROUND OF THE DISCLOSURE

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods for use in a variety of body lumens, including but not limited to coronary, peripheral, and other arteries, and other body lumens.

SUMMARY OF THE DISCLOSURE

In one aspect, a tissue-removing catheter generally comprises an elongate catheter body configured for insertion into a body lumen of a subject. The catheter body has opposite distal and proximal ends, a longitudinal axis extending between the distal and proximal ends, and an interior tissue-transport passage extending along the longitudinal axis. A cutter located generally at the distal end of the catheter body for rotation generally about the longitudinal axis of the catheter body has a proximal end portion, a distal end portion, and a longitudinal axis extending between the proximal and distal end portions. The cutter includes an annular cutting edge at the distal end portion of the cutter for removing tissue from the body lumen, an axial cavity defined by an interior surface of the cutter extending proximally from the annular cutting edge toward the proximal end portion of the cutter, and an opening extending from the central cavity through the cutter to allow tissue removed from the body lumen by the annular cutting edge to pass proximally through the opening toward the tissue-transport passage of the catheter body. A screw blade extends longitudinally within the interior passage of the catheter body and is rotatable about its axis relative to the catheter body. The screw blade includes an external helical thread for transporting removed tissue proximally within the tissue-transport passage as the screw blade rotates about its axis. The screw blade defines an interior driveshaft passage extending longitudinally therein. A cutter driveshaft extends longitudinally within the driveshaft passage of the screw blade and is rotatable about its axis relative to the screw blade. The cutter driveshaft has a distal end portion operatively coupled to the cutter for driving rotation of the cutter.

In another aspect, a tissue-removing catheter generally comprises an elongate catheter body configured for insertion into a body lumen of a subject. The catheter body has opposite distal and proximal ends, a longitudinal axis extending between the distal and proximal ends, and an interior driveshaft passage extending along the longitudinal axis. A cutter is located generally at the distal end of the catheter body for rotation generally about the longitudinal axis of the catheter body. The cutter has a proximal end portion, a distal end portion, and a longitudinal axis extending between the proximal and distal end portions. The cutter includes an annular cutting edge at the distal end portion of the cutter for removing tissue from the body lumen, and an axial cavity defined by an interior surface of the cutter extending axially from the annular cutting edge through the distal end portion of the cutter to allow tissue removed from the body lumen by the annular cutting edge to pass proximally through the cutter. A cutter driveshaft extends longitudinally within the driveshaft passage of the catheter body and is rotatable about its axis relative to the catheter body. The cutter driveshaft has a distal end portion operatively coupled to the cutter for driving rotation of the cutter. The cutter driveshaft defines a tissue-transport passage extending longitudinally therein in communication with the axial cavity of the cutter. A screw blade extends longitudinally within the tissue-transport passage of the cutter driveshaft and through the axial cavity of the cutter. The screw blade is rotatable about its axis relative to the cutter driveshaft and includes an external helical thread for transporting removed tissue proximally within the tissue-transport passage as the screw blade rotates about its axis.

In yet another aspect, a tissue-removing catheter generally comprises an elongate catheter body configured for insertion into a body lumen of a subject. The catheter body has opposite distal and proximal ends, a longitudinal axis extending between the distal and proximal ends, and an interior driveshaft passage extending along the longitudinal axis. A cutter is located generally at the distal end of the catheter body for rotation generally about the longitudinal axis of the catheter body. The cutter has a proximal end portion, a distal end portion, and a longitudinal axis extending between the proximal and distal end portions. The cutter includes an annular cutting edge at the distal end portion of the cutter for removing tissue from the body lumen, and an axial cavity defined by an interior surface of the cutter extending axially from the annular cutting edge through the distal end portion of the cutter to allow tissue removed from the body lumen by the annular cutting edge to pass proximally through the cutter. A cutter driveshaft extends longitudinally within the driveshaft passage of the catheter body and is rotatable about its axis relative to the catheter body. The cutter driveshaft has a distal end portion operatively coupled to the cutter for driving rotation of the cutter. The cutter driveshaft defines a tissue-transport passage extending longitudinally therein in communication with the axial cavity of the cutter. A screw blade extends longitudinally within the tissue-transport passage of the cutter driveshaft and through the axial cavity of the cutter. The screw blade is rotatable about its axis relative to the cutter driveshaft and includes a distal end and an external helical thread for transporting removed tissue proximally within the tissue-transport passage as the screw blade rotates about its axis. The cutter driveshaft is selectively movable longitudinally within the catheter body, independently of the screw blade, for deploying and retracting the cutter. The screw blade is selectively movable longitudinally within the tissue-transport passage from a proximal, tissue-collection position, in which the distal end is spaced proximally from the annular cutting edge of the cutter to allow for tissue removed by the cutter to collect in the tissue-transport passage between the screw blade the cutting edge, to a distal, tissue-conveying position, in which the distal end of the screw blade is closer to the annular cutting edge of the cutter to transport tissue in the tissue collection chamber proximally within the tissue-transport passage as the screw blade is rotated.

In another aspect, a tissue-removing catheter generally comprises an elongate catheter body configured for insertion into a body lumen of a subject. The catheter body has opposite distal and proximal ends, a longitudinal axis extending between the distal and proximal ends. A cutter located generally at the distal end of the catheter body for rotation generally about the longitudinal axis of the catheter body has a proximal end portion, a distal end portion, and a longitudinal axis extending between the proximal and distal end portions. An interior surface defines a tissue-transport passage extending longitudinally within the catheter body from generally adjacent the cutter to a location proximal of the cutter. The interior tissue-transport passage has a maximum interior diameter. A screw blade extends longitudinally within the interior tissue-transport passage and is rotatable about its axis within the tissue-transport passage. The screw blade includes an external helical thread for transporting removed tissue proximally within the tissue-transport passage as the screw blade rotates about its axis. The external helical thread has a maximum outer diameter. A radial gap between the thread on the screw blade and the interior surface defining the tissue-transport passage is sized so that removed tissue is pinched between the thread and the interior surface, without substantially macerating the tissue, to facilitate proximal movement of the tissue.

Other objects and features will be in part apparent and in part pointed out hereinafter.

BRIEF DESCRIPTION OF THE DRAWINGS

FIG. 3 is a longitudinal section of the distal end portion of the tissue-removing catheter of FIG. 2A;

FIG. 4A is an enlarged side elevation of the distal end portion of the tissue-removing catheter, with the cutter of the tissue-removing catheter in a deployed, cutting position;

FIG. 6A is an exploded perspective of the distal end portion of the tissue-removing catheter;

FIG. 13A is an enlarged side elevation of the distal end portion of the tissue-removing catheter of FIG. 10, with the cutter of the tissue-removing catheter in a deployed, cutting position;

FIG. 15A is an exploded perspective of the distal end portion of the tissue-removing catheter of FIG. 10;

FIG. 15B is an enlarged, exploded perspective of the cutter housing of the tissue-removing catheter of FIG. 10;

FIG. 19 is fragmentary perspective of a third embodiment of a tissue-removing catheter;

Corresponding reference characters indicate corresponding parts throughout the drawings.

DETAILED DESCRIPTION OF THE DRAWINGS

Figure 1:
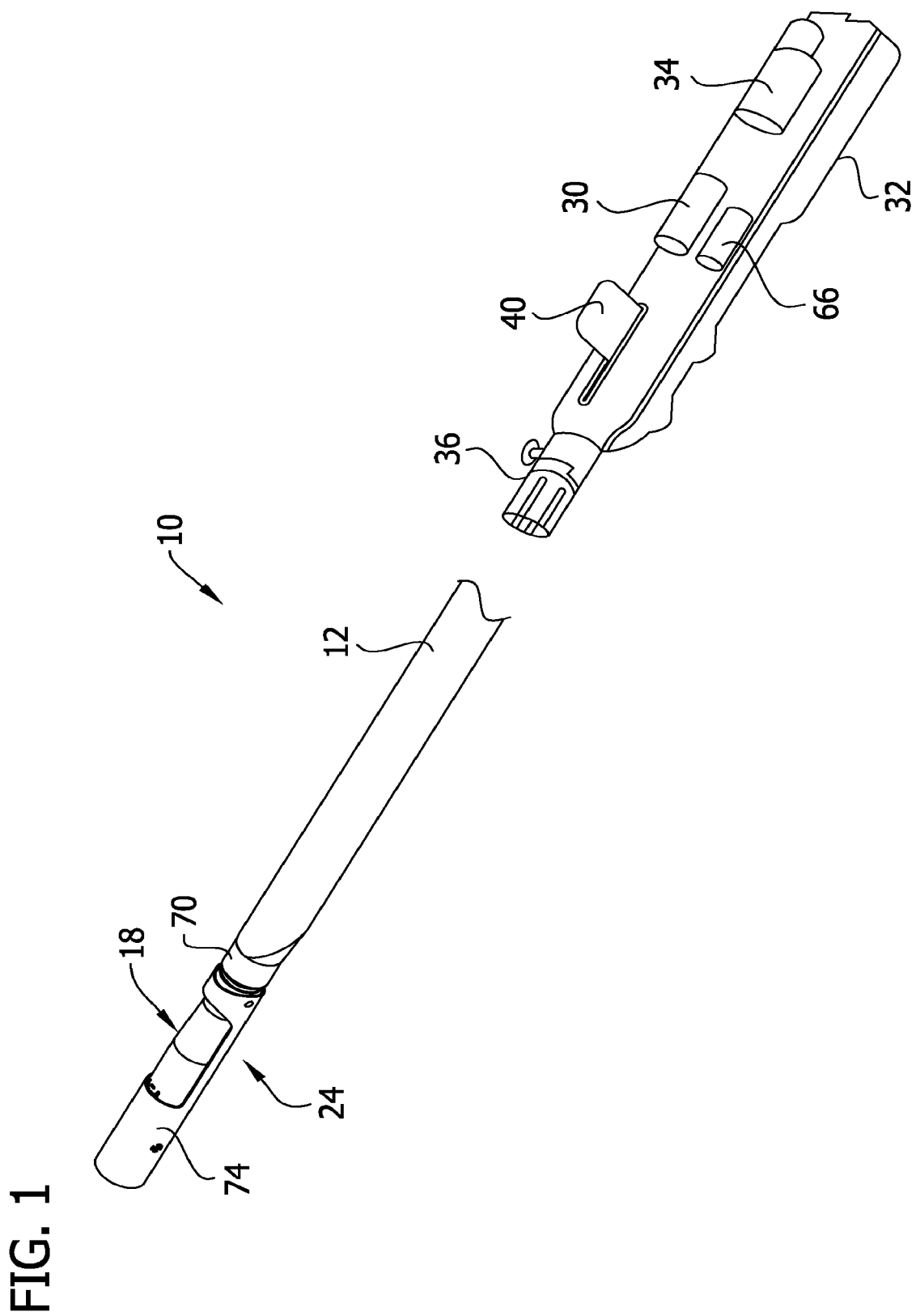
FIG. 1 is a fragmentary perspective of an embodiment of a tissue-removing catheter.

Referring now to the drawings, several embodiments of a tissue-removing catheter for removing tissue from a body lumen are disclosed. In particular, the illustrated catheter embodiments are suitable for removing tissue from a body lumen, and are particularly suitable for removing (i.e., excising) plaque tissue from a blood vessel (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 4B:
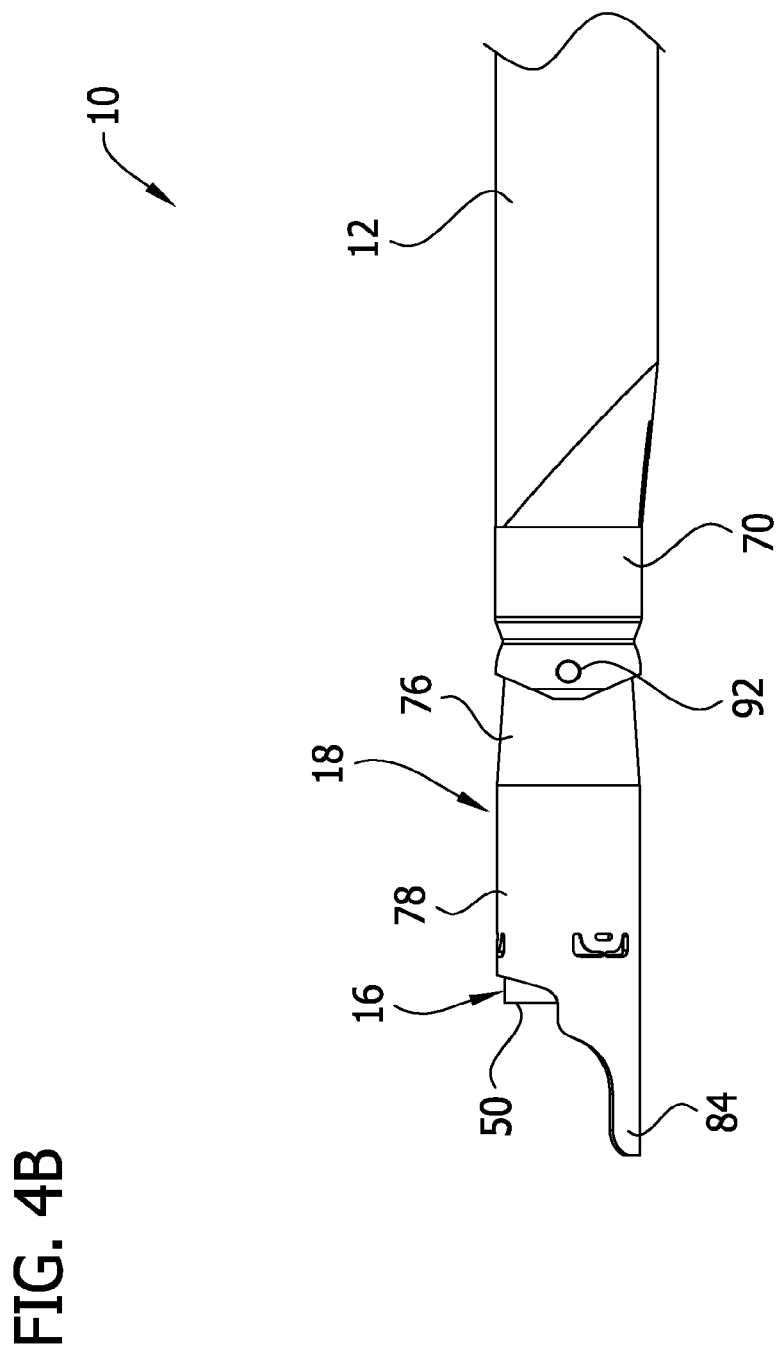
FIG. 4B is similar to FIG. 4A, except the cutter housing is removed to show hidden components.
Figure 5:
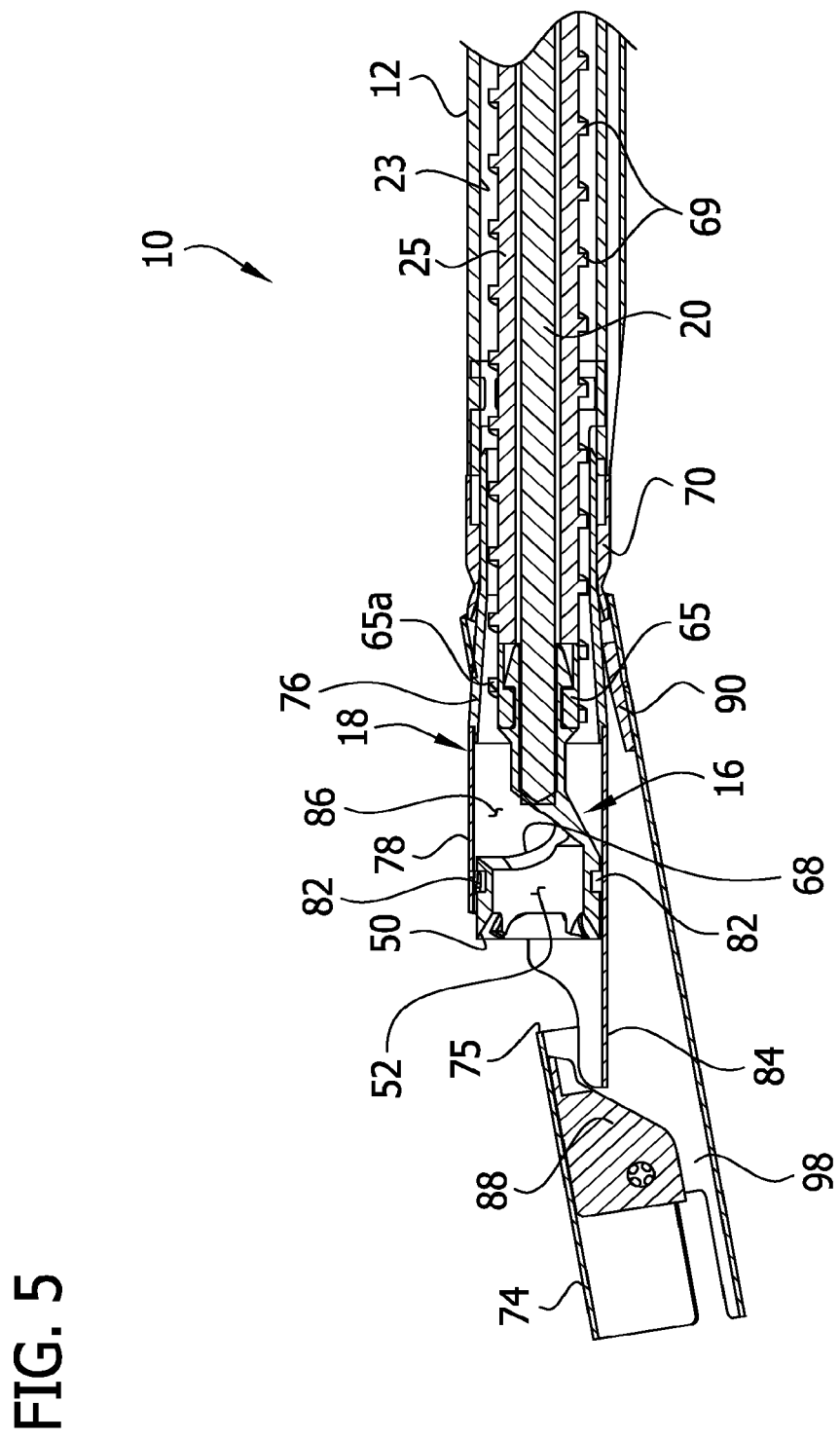
FIG. 5 is a longitudinal section of the distal end portion of the tissue-removing catheter of FIG. 4A.
Figure 6B:
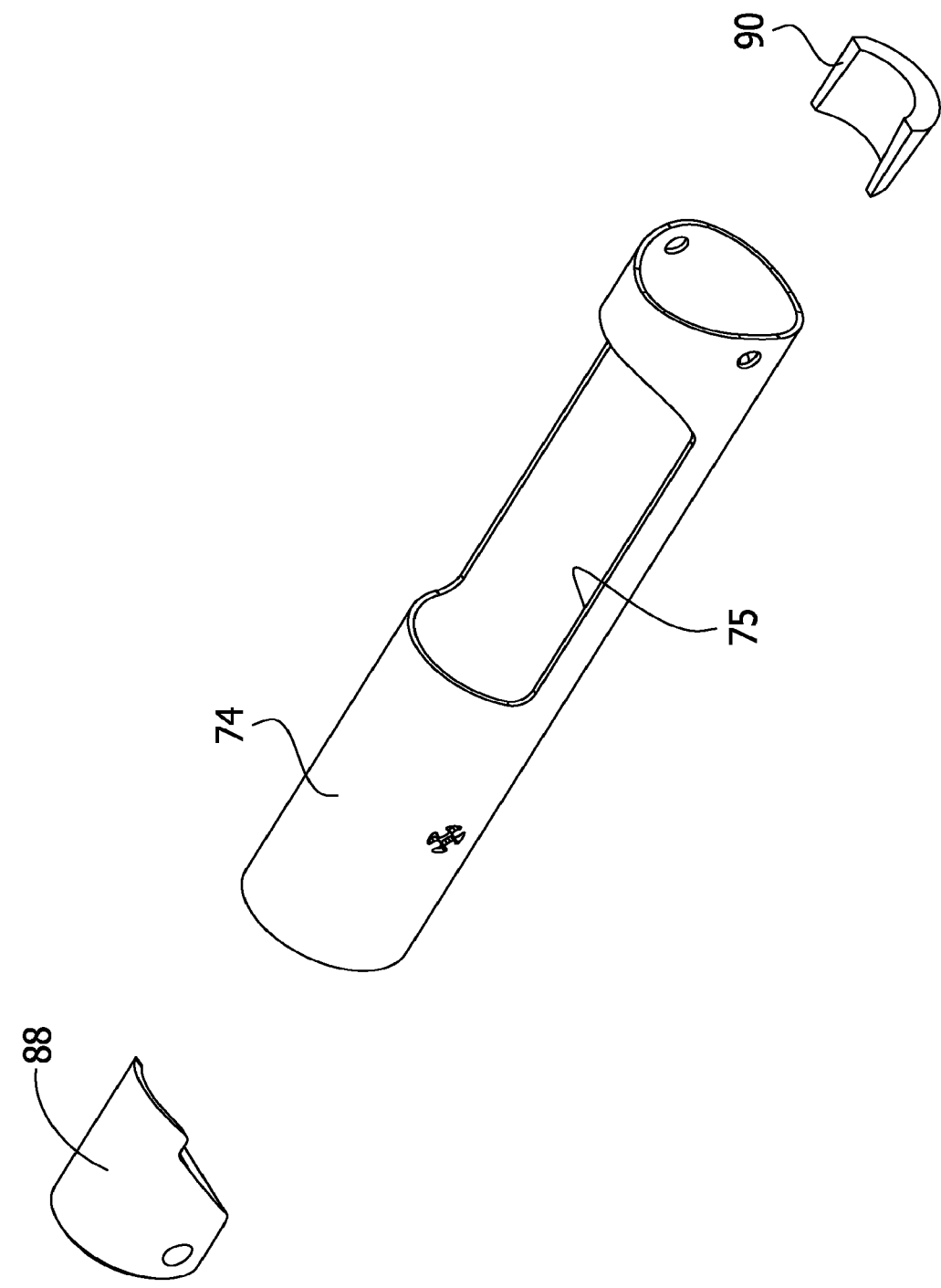
FIG. 6B is an enlarged, exploded perspective of the cutter housing of the tissue-removing catheter.

Referring now to FIGS. 1-9, a first embodiment of an atherectomy catheter (broadly, a tissue-removing catheter) is generally indicated by reference numeral 10. Briefly, the atherectomy catheter 10 includes an elongate tubular catheter body 12 having opposite proximal and distal ends, a central longitudinal axis $LA_1$ (FIG. 2A) extending between the distal and proximal ends. Referring to FIGS. 3 and 5, a rotatable cutter, generally indicated at 16, is supported by the distal end of the catheter body 12 for removing tissue from a body lumen. In particular, in the illustrated embodiment the cutter 16 is operatively connected to a cutter adaptor, generally indicated at 18. The catheter 10 also includes a cutter driveshaft 20 (FIGS. 3 and 5), which drives rotation of the cutter 16, and a separate screw conveyor, generally indicated at 22 (also known as an auger conveyor), which transports or moves removed tissue proximally within the catheter body 12. The screw conveyor 22 includes an internal tissue-transport passage 23 (FIGS. 3 and 5) extending generally along the longitudinal axis $LA_1$ of the catheter body 12, and a screw blade 25 (or flighting) rotatable about its longitudinal axis within the tissue-transport passage. A deployment mechanism, generally indicated at 24, configures the atherectomy catheter 10 between a non-deployed position in which the cutter is not exposed for cutting (FIGS. 1, 2A and 3) and a deployed position in which the cutter is exposed for cutting (FIGS. 4A and 5).

Referring still to FIG. 1, the catheter body 12 is configured (e.g., sized and shaped) for intravascular introduction into the target artery, although as explained above, the catheter body may be configured for intraluminal introduction into other target body lumens other than a target artery. Although not illustrated, the catheter 10 may be configured for introduction of the catheter body 12 over a guidewire to a target site within the vasculature. In particular, the catheter 10 may be configured for "over-the-wire" introduction when a guidewire channel extends fully through the catheter body 12 or for "rapid exchange" introduction where the guidewire channel extends only through a distal portion of the catheter body. In other cases, it may be possible to provide a fixed or integral coil tip or guidewire tip on the distal portion of the catheter 10 or even dispense with the guidewire entirely. Moreover, a flexible distal tip 27 (FIG. 2A) may be secured to the distal end of the illustrated catheter to facilitate insertion of the catheter. For convenience of illustration, guidewires will not be shown in any embodiment, but it should be appreciated that they can be incorporated into any of these embodiments.

The dimensions and other physical characteristics of the catheter body 12 may vary depending on the artery (or other body lumen) of the subject which is to be accessed. The catheter body 12 is generally flexible and may in one embodiment have a length in the range from 50 cm to 200 cm and an outer diameter in the range from 1 French to 12 French (0.33 mm: 1 French), such as from 3 French to 9 French. The catheter body 12 may be composed of an organic polymer which is fabricated by extrusion techniques. Suitable polymers include polyvinylchloride, polyurethanes, polyesters, polytetrafluoroethylenes (PTFE), silicone rubbers, natural rubbers, and the like. Optionally, the catheter body 12 may be reinforced with a braid, helical wires, coils, axial filaments, or the like, in order to increase rotational strength, column strength, toughness, pushability, and the like. For example, the catheter body 12 may include a torque tube, as is generally known in the art. The outer diameter of the catheter body 12 can be modified by heat expansion and shrinkage using conventional techniques. It will be appreciated that the construction and dimensions of the catheter body may be other than described without departing from the scope of the present invention.

The catheter body 12 of the present embodiment may include an urging mechanism (not shown) to urge the cutter into engagement with the body lumen during treatment. For example, the urging mechanism may comprise a portion of the catheter body adjacent to and proximal of the cutter that is biased to (e.g., permanently deformed in) a double-bent or double-curved shape to urge the cutter toward a wall of a body lumen to enhance treatment. A suitable urging mechanism is disclosed in U.S. Pat. No. 7,708,749, the relevant teaching of which is hereby incorporated by reference. In other embodiments, the urging mechanism may take many other suitable forms. The catheter may have no urging mechanism without departing from the scope of the present invention.

Referring to FIGS. 3 and 5, as set forth above, the catheter 10 includes the rotatable cutter 16 and the cutter driveshaft 20 for imparting rotation of the cutter. The driveshaft 20 extends along a Longitudinal driveshaft passage 26 in the screw blade 25 so that the driveshaft is generally coaxial with the screw blade. As explained below, in the illustrated embodiment the driveshaft 20 is rotatable about its axis independently of the screw blade 25, and the screw blade is rotatable about its axis independently of the driveshaft. A distal end portion of the driveshaft 20 is operatively connected to the rotatable cutter 16 for selectively driving rotation of the cutter generally about the longitudinal axis $LA_1$ of the catheter body 12. In the illustrated embodiment, the distal end portion of the driveshaft 20 is fixedly secured to the cutter 16. The shank of the driveshaft 20 is generally flexible and may be formed from one or more coils (e.g., stainless steel coil(s)), or a torque tube (e.g., a polyimide tube with a layer of braided stainless steel wire embedded therein). The shank of the driveshaft 20 may have a very high torsional stiffness and sufficient tensile strength, but be generally laterally flexible. Depending upon the desired torque transmission, diameter and flexibility, any of a variety of other materials and constructions may also be used.

Referring to FIG. 1, the proximal end of the driveshaft 20 is operably connected to a cutter motor 30 (broadly, a cutter driver) to impart rotation of the driveshaft 20 relative to catheter body 12. In one example, the cutter motor 30 is disposed within a handle 32 (shown with a cover removed in FIG. 1) that is releasably connectable to the proximal end of the catheter 10. It is envisioned that a handle may be permanently attached to the proximal end of the catheter. In addition to the cutter motor 30, the handle 32 may, for example, house a power source 34 (e.g., batteries) for the cutter motor 30, a microswitch (not shown) for activating cutter motor, and a catheter connector 36 for connecting the motor to the proximal end portion of the driveshaft 20. In some embodiments, the cutter motor 30 can rotate the driveshaft 20 between 1,000 rpm and 10,000 rpm or more, if desired. As explained in more detail below, the handle 32 may include one or more input devices, such as lever 40, which controls the major operations of the catheter 10, such as axial movement of the driveshaft 20 to actuate the deployment mechanism 24, and rotation of the driveshaft 20 and the cutter 16 via the cutter driver 30. It is understood that the driveshaft 20 may be driven in other ways without departing from the scope of the present invention.

Figure 7:
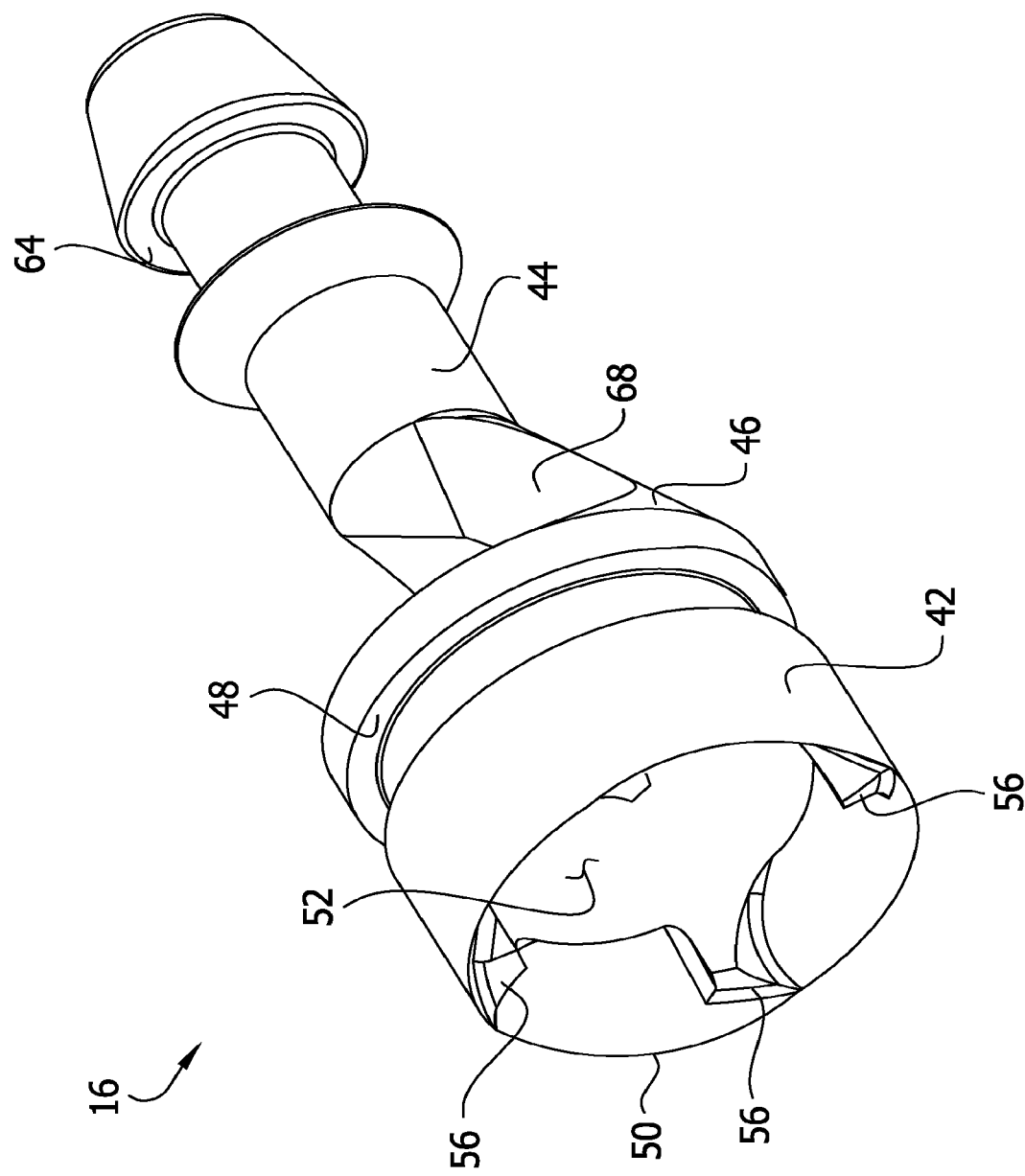
FIG. 7 is an enlarged, front perspective of the cutter of the tissue-removing catheter.
Figure 8:
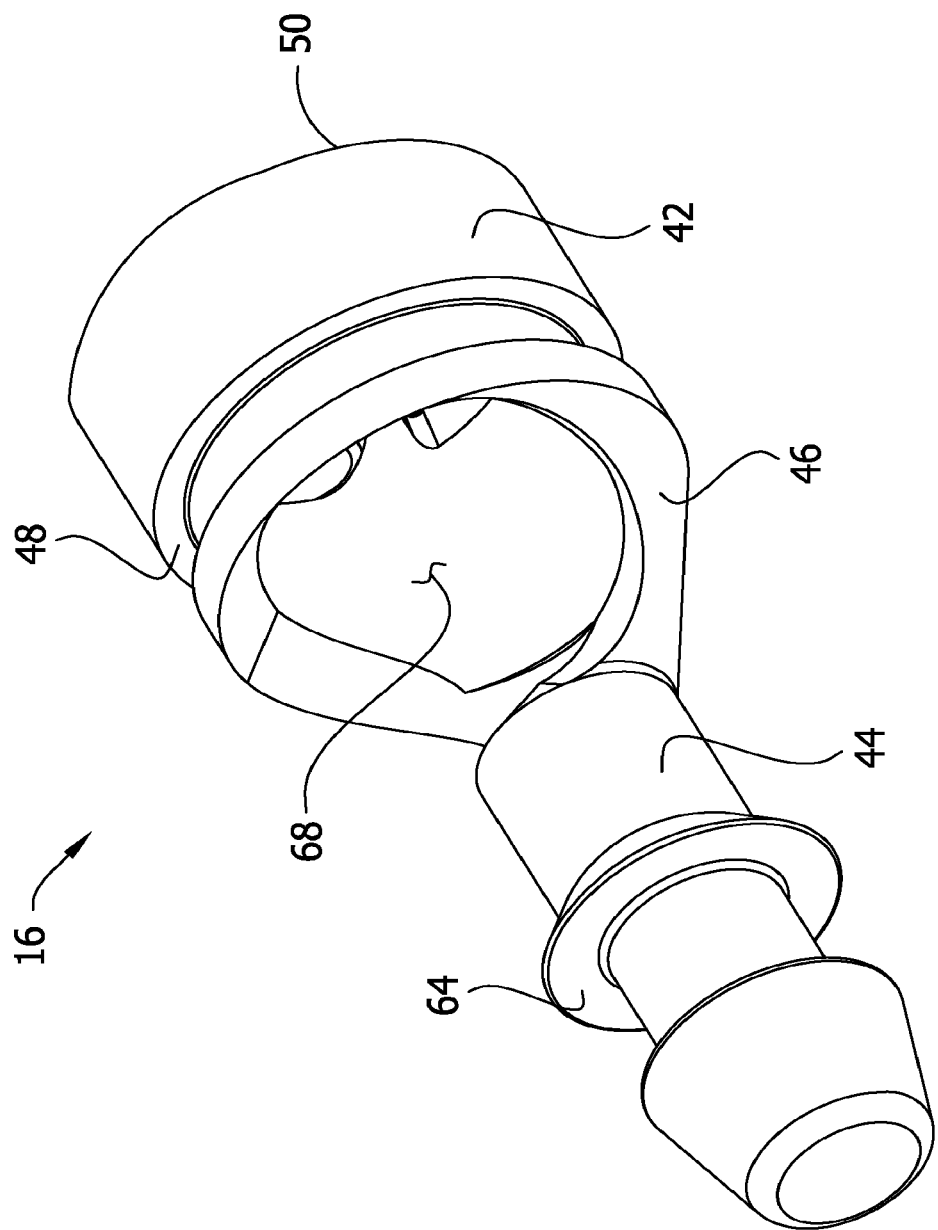
FIG. 8 is an enlarged, rear perspective of the cutter of the tissue-removing catheter.
Figure 9:
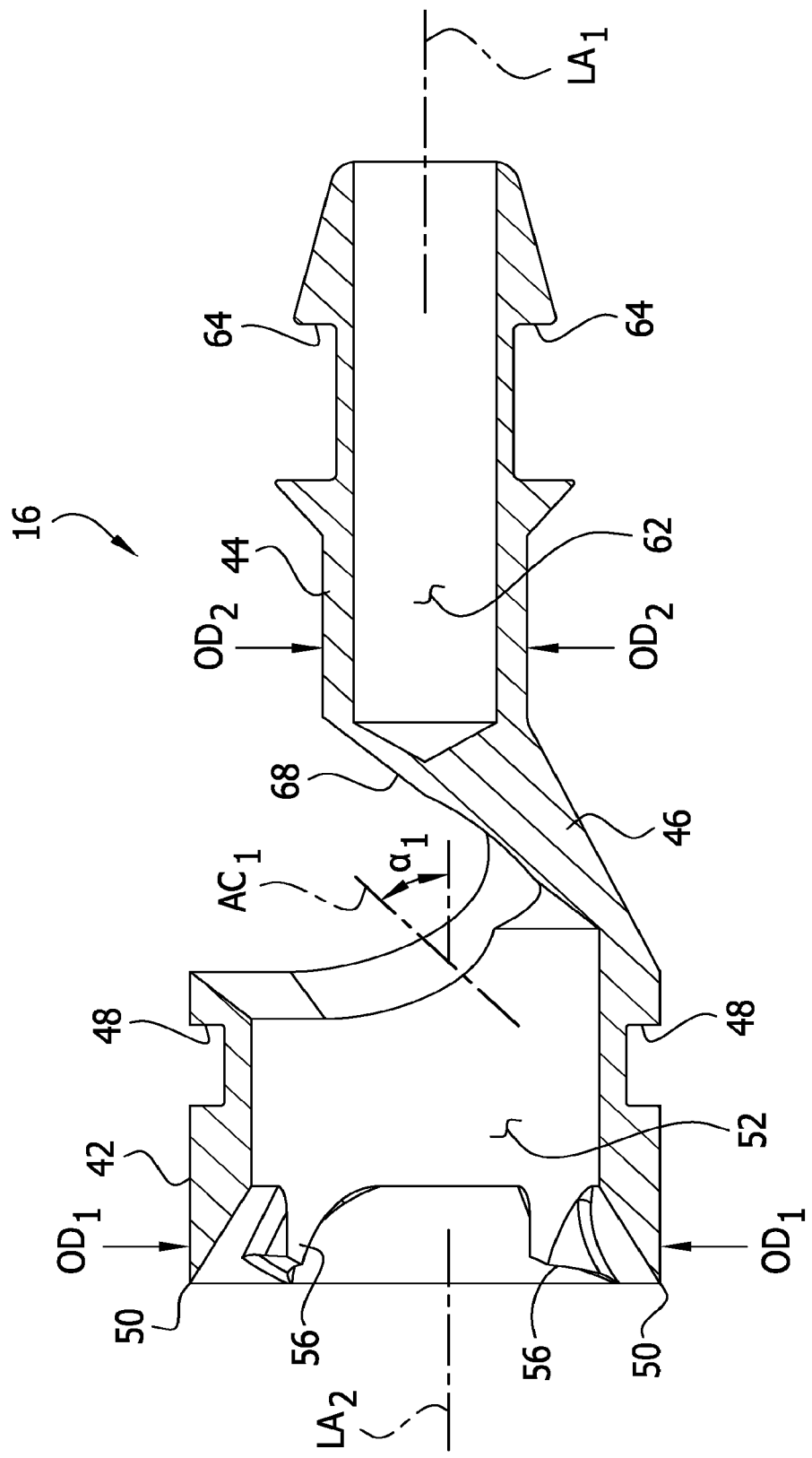
FIG. 9 is an enlarged, longitudinal section of the cutter.

As seen best in FIGS. 7-9, the rotatable cutter 16 has opposite proximal and distal ends and a longitudinal axis $LA_2$ extending therebetween. The cutter 16 has a generally cylindrical distal cutting portion 42, a proximal stem 44 (broadly, a driveshaft-connection portion), and a transitional portion 46 intermediate the distal cutting portion and the stem. Referring to FIG. 9, the distal cutting portion 42 has an outer cross-sectional dimension $OD_1$ (e.g., an outer diameter) that is greater than an outer cross-sectional dimension $OD_2$ (e.g., an outer diameter) of the stem 44, and the exterior of the transitional portion 46 tapers (e.g., necks down) longitudinally from the distal cutting portion to the stem. For reasons explained below, the exterior surface of the distal cutting portion 42 has a circumferential groove 48 formed therein. The cutter 16 may be formed as a single, one-piece construction, or may be formed from separate components secured to one another in a suitable manner, such as welding, soldering, adhesives, mechanical interference fit, threaded engagement and the like. As a non-limiting example, the cutter 16 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Referring still to FIGS. 7-9, the distal cutting portion 42 of the cutter 16 includes an annular cutting edge 50 at the distal end thereof, and an axial cavity 52, defined by an interior surface of the cutter 16, extending from the cutting edge toward the stem 44 of the cutter. In one non-limiting example, the annular cutting edge 50 is beveled from an exterior surface of the cutter toward the interior surface to define the sharp, distal cutting edge. The cutting edge 50 may be formed separately from the distal cutting portion 42 of cutter 16 and attached thereto, or the cutting edge may be formed integrally with the distal cutting portion of cutter. In the embodiment illustrated in FIGS. 7-9, the beveled, annular cutting edge 50 includes one or more raised elements 56 (e.g., breakers), although the cutter 16 may not include the raised elements without departing from the scope of the present invention. In the illustrated embodiment, four raised elements 56 are formed on the beveled, annular cutting edge 50, although in other embodiments more than four or fewer than four raised elements may be present. During removal of tissue from the target body lumen, the raised elements 56 may produce a hammer-like impact against the tissue to be removed as the cutter 16 is rotated. In the case where the tissue to be removed has brittle characteristics (e.g., has become calcified), the tissue will be crushed into smaller particles thereby facilitating its removal. Repeated rotation of cutter 16 will produce repeated hammer-like blows of the cutter raised elements 56 against the tissue to be removed. Exemplary raised elements 56 are disclosed in U.S. Published Patent Application No. 2011/0130777 (Ser. No. 12/958,488), filed Dec. 2, 2010, the entirety of which is incorporated by reference herein. In other embodiments, the annular cutting edge 50 may have a generally smooth surface. The cutting edge may be of other configurations without departing from the scope of the present invention.

The stem 44 connects the cutter 16 to the distal end of the cutter driveshaft 20 so that rotation of the driveshaft imparts rotation of the cutter 16 about its longitudinal axis $LA_2$ (i.e., the rotational axis of the cutter is coincident with the central longitudinal axis of the cutter). In the illustrated embodiment, and as shown in FIG. 9, a central longitudinal axis $LA_3$ of the stem 44 is coincident with the central longitudinal axis $LA_2$ of the cutter 16. The stem 44 defines a bore 62, having a central axis coincident with the central longitudinal axis of the stem, in which the distal end of the driveshaft 20 is secured. For example, the distal end of the driveshaft 20 may be secured in the bore 62 by soldering, welding, adhesive, press-fit interference, crimping, or in other ways. As explained in more detail below, the stem 44 also includes a circumferential groove 64 in which an internal, annular bearing member 65 (FIGS. 3 and 5) adjacent the distal end of the screw blade 25 is received so that the cutter 16 is rotatable about its axis $LA_2$ relative to the screw blade, and vice versa.

As set forth above, the tissue removed from the blood vessel by the cutting edge 50 passes proximally through the cutter 16, toward the tissue-transport passage 23 of the catheter body 12. In the illustrated embodiment, the cutter 16 has an eccentric opening 68 in communication with the axial cavity 52 to allow removed tissue to pass through the cutter. Together, the eccentric opening 68 and the axial cavity 52 define a tissue passage extending through the cutter 16. Thus, as can be seen from FIG. 5, as the tissue is being removed, it enters the axial cavity 52, and then passes through the eccentric opening 68 and into the cutter adaptor 18, where it can be picked up by the screw blade 25 (or other transport mechanism), and transported proximally within tissue-transport passage 23. Referring to FIG. 9, the eccentric opening 68 in the cutter 16 is offset with respect to the longitudinal axis $LA_2$ (and rotational axis) of the cutter. The eccentric opening 68 is shaped so that when viewed from the distal end of the cutter 16 looking proximally, the eccentric opening extends around the longitudinal axis $LA_2$ in an arc and does not intersect the longitudinal axis of the cutter. In the illustrated embodiment (see best in FIGS. 7-9), the eccentric opening 68 extends through the tapered transitional portion 46 of the cutter 16, so that the interior surface of transitional portion 46 through which the eccentric opening extends (as defined by an axis $AC_1$ that is parallel to the interior surface of the transitional portion 46) extends at an angle $\alpha_1$ that is neither coincident nor parallel with the longitudinal axis $LA_2$ (and rotational axis) of the cutter. As a non-limiting example, the offset angle $\alpha_1$ may measure from about 15 degrees to about 60 degrees, and in one example, about 45 degrees, from the longitudinal axis $LA_2$ (and rotational axis) of the cutter 16. It is understood that the cutter 16 may be of other configurations in other embodiments of the catheter without departing from the scope of the present invention.

Referring to FIGS. 3 and 5, the screw blade 25 includes a helical thread 69 on the exterior of its shank and extending longitudinally thereon so that rotation of the screw blade about its axis transports removed tissue proximally within the tissue-transport passage 23. In the illustrated embodiment, the thread 69 is a right-handed thread (as viewed from the proximal end of the driveshaft screw blade 25), so that rotation of the screw blade clockwise (as viewed from the proximal end of the screw blade) relative to the tissue-transport passage 23 transports the tissue proximally. The tissue transport passage 23 and the screw blade thread 69 may extend back to the proximal end portion of the catheter body 12 and may empty into a tissue receptacle (not shown). The tissue transport passage 23 and screw blade thread 69 may stop short of the proximal end portion of the catheter body 12. The thread 69 may be formed on the shank of the screw blade 25 in a suitable manner.

In one example, shown in FIGS. 3 and 5, the cross-sectional dimension of the tissue-transport passage 23 (e.g., inner diameter of the catheter body 12) is slightly greater than the major diameter of the exterior thread 69 on the screw blade 25 so that there is a small radial gap (or play) between the thread on the screw blade and interior surface of the body 12 defining the tissue-transport passage 23. In this example, the radial gap is such so as not to inhibit or impede rotation and axial movement of the screw blade 25 in tissue-transport passage 23, and at the same time, substantially inhibit tissue from passing between the thread 69 on the screw blade 25 and the interior surface defining the tissue-transport passage. For example, the diameter of the tissue-transport passage 23 may be from about 0.001 in (0.025 mm) to about 0.005 in (0.127 mm) greater than the major diameter of the exterior thread 69. In another embodiment, the radial gap between the thread 69 on the screw blade 25 and interior surface of the body 12 defining the tissue-transport passage 23 is sized so that removed tissue is pinched between the thread and the interior surface, without substantially macerating the tissue, to facilitate proximal movement of the tissue intact. For this embodiment, the radial gap may measure from greater than about 0.005 in (0.127 mm) to about 0.020 in (0.508 mm), and in one example, from about 0.010 in (0.245 mm) to about 0.015 in (0.381 mm). It is understood that in some embodiments the screw conveyor 22 may be omitted without departing from the scope of the present invention.

As set forth above, the annular bearing member 65 on the screw blade 25 is received in the circumferential groove 64 on the cutter 16 so that the cutter is rotatable about its axis $LA_2$ relative to the screw blade, and the screw blade is rotatable relative to the cutter. In the illustrated embodiment, the bearing member 65 (e.g., a bearing fitting or ferrule) is fixedly secured to the distal end of the screw blade 25. This coupling inhibits relative axial movement of the cutter 16 and the screw blade 25, while allowing the cutter and the screw blade to rotate about their respective axes relative to one another. The bearing member 65 and the screw blade 25 may be formed as a single, one-piece construction, or may be formed from separate components secured to one another in a suitable manner, such as welding, soldering, adhesives, mechanical interference fit, threaded engagement and the like. In the present illustrated embodiment, the bearing member 65 includes a helical, exterior thread 65a (FIGS. 3 and 5) running along the length of the bearing member to further facilitate proximal transport of removed tissue. In the illustrated embodiment (shown best in FIGS. 3 and 5), the exterior thread 65a on the bearing member 65 is aligned (or mates) with the thread 69 on the screw blade 25 to form a substantially continuous thread extending from the screw blade to the bearing member. In one example, the pitch of the bearing member thread 65a is the same pitch of the screw blade thread 69, although the pitches may be different. In at least some embodiments, the cutter 16 may be coupled to screw blade 25 in other ways, or the cutter may not be directly coupled to the screw blade, without departing from the scope of the present invention.

Referring to FIG. 1, the proximal end of the screw blade 25 is operably connected to a conveyor motor 66 (broadly, a conveyor driver) to impart rotation of the screw blade 25 relative to catheter body 12. In one example, the conveyor motor 66 is disposed within the handle 32 (shown with a cover removed in FIG. 1) that is connected to the proximal end of the catheter 10. The power source 34 (e.g., batteries) may power the conveyor motor 66 in addition to the cutter motor 30, or a different power source may be provided. A different microswitch (not shown), actuated by the lever 40, may be used to activate the conveyor motor 66. The lever 40 may control axial movement of the screw blade 25 (together with the driveshaft 20), and may actuate rotation of the screw blade via the conveyor motor 66. As explained below, in one embodiment, the conveyor motor 66 is operable independently of the cutter motor 30 to allow for transportation of removed tissue even if the cutter 16 is not in operation. Moreover, the conveyor motor 66 may rotate the screw blade 25 in a direction opposite that of the cutter driveshaft 20 and the cutter 16. The lever 40 may be configured to operate the conveyor motor 66 independently of the cutter motor 30 (e.g., the lever may be movable to different positions to separately operate the conveyor and cutter motors), or the handle 32 may include a separate input device (e.g., a button or other actuator) for operating the conveyor motor independently of the cutter motor. In another embodiment, the cutter driveshaft 20 and the screw blade 25 may be driven by the same driver (e.g., motor), such as motor 30. For example, the catheter may include suitable gearing for transmitting torque from the driver to both the driveshaft 20 and the screw blade 25. It is understood that the screw blade 25 may be driven in other ways without departing from the scope of the present invention.

As set forth above, the catheter 10 includes the deployment mechanism 24 for configuring the cutter 16 between the non-deployed position (FIGS. 1 and 3) and the deployed position (FIGS. 4A and 5). The deployment mechanism 24 is connected to a deployment adaptor 70 at the distal end of the catheter body 12, and the deployment adaptor is secured to a collar 71 (e.g., a laser cut collar) that is secured to the distal end of the catheter body. For purposes of the disclosure, the deployment adaptor 70 and the collar 71 are considered part of the catheter body 12, and in particular, part of the distal end of the catheter body. In the illustrated embodiment, the deployment mechanism 24 includes a cutter housing 74, defining a cutter window 75, hingedly attached to the deployment adaptor 70 at the distal end portion of the catheter body 12.

The cutter adaptor 18 is axially (i.e., proximally and distally) moveable relative to the cutter housing 74, whereby proximal movement of the cutter adaptor drives the cutter housing to pivot about its hinge axis $A_H$ (FIG. 4A) to open the deployment mechanism 24 and expose the cutting edge 50 through the cutter window 75 (FIG. 5), and distal movement of the cutter adaptor drives the cutter housing to pivot about its hinge axis to close the deployment mechanism so that cutting edge is non-deployed in the cutter housing (FIGS. 2 and 3). The cutter adaptor 18 is axially moveable relative to the cutter housing 74 (and the catheter body 12) by axially moving the driveshaft 20 and/or the screw blade 25, which imparts axial movement to the cutter 16. Accordingly, the cutter adaptor 18 moves axially with the cutter 16, which is conjointly moveable by the driveshaft 20. In one embodiment, the driveshaft 20 is axially moveable relative to the catheter body 12 by actuating the lever 40 on the handle 32, which may also actuate the motor 30 to drive rotation of the driveshaft and the cutter 16.

Referring to FIGS. 2-6B, in the illustrated embodiment, the cutter adaptor 18 includes a proximal tube piece 76 and a distal, rotational bearing member 78 supporting the cutter 16 (together defining an adaptor tube or adaptor tube assembly in which the cutter is received). The bearing member 78 is received in the cutter housing 74 and is axially slidable therein. In particular, in the illustrated embodiment, the bearing member 78 has an exterior surface having an arcuate cross-sectional shape that is generally complementary to the interior arcuate cross-sectional shape of the cutter housing 74, so that the bearing member nests in the cutter housing. In the illustrated embodiment, the components of the cutter adaptor 18 are formed as separate components and secured to one another by in a suitable fashion, such as by adhesive, welding, fasteners, or the like. Alternatively, selective components (including all of the components) may be formed integrally as a single, one-piece component. For example, the proximal tube pieces 76 and the bearing member 78 may be formed as a single, one-piece component. The respective components of the cutter adaptor 18, including the distal bearing member 78, the proximal tube piece 76, and the cutter housing 74 may be formed from stainless steel or other biocompatible material. In general, the cutter housing 74 may be more rigid than the catheter body 12.

The rotational bearing member 78 is configured to allow rotation of the cutter 16 generally about the longitudinal axis $LA_1$ of the catheter body 12 relative to the cutter adaptor 18, while substantially inhibiting axial movement of the cutter relative to the cutter adaptor, so that the cutter adaptor moves axially with the cutter. The rotational bearing member 78 also retains the cutter 16 in proper position relative to the cutter adaptor 18 as the cutter is rotated by the driveshaft 20. To this end, the bearing member 78 has an internal support surface having an arcuate cross-sectional shape that is generally complementary to the exterior shape of the annular cutting edge 50 of the cutter 16 for supporting the cutter and the distal tube piece. In the illustrated embodiment (FIGS. 3 and 5), the bearing member 78 includes pins 82 received in the circumferential groove 48 in the exterior surface of the cutter 16. The cutter adaptor 18, more specifically, the rotational bearing member 78 includes a tongue 84 extending distally relative to the cutting edge 50. As explained below, the tongue 84 interacts with a closing ramp follower 88 of the cutter housing 74 when the cutter adaptor 18 is moved distally to facilitate retracting the cutter 16 within the cutter, housing. The rotational bearing member 78 may be of other configurations and types without departing from the scope of the present invention.

Referring to FIGS. 3-5, the proximal tube piece 76 and the bearing member 78 together define an internal passage 86 of the cutter adaptor 18 in which a portion of the cutter 16 (e.g., the transitional and proximal portions 46, 44 of the cutter) and a portion of the driveshaft 20 (e.g., the distal end portion of the driveshaft) are received. As shown in FIG. 2B, the exterior of the proximal tube piece 76 has a transitional portion tapering proximally from the rotational bearing member 78, and proximal portion that is received in the distal end portion of the catheter body 12 to connect the internal passage 86 of the adaptor tube assembly 18 with the tissue-transport passage 23. As explained below, the exterior of the proximal tube piece 76 interacts with an opening ramp follower 90 of the cutter housing 74 when the cutter adaptor 18 is moved proximally to facilitate opening of the deployment mechanism 24. The opening ramp follower 90 and closing ramp follower 88 remain in operative contact with the adaptor tube assembly 18 (which functions as a camming element, as described below) in all relative positions of the cutter housing and adaptor tube assembly.

Figure 2A:
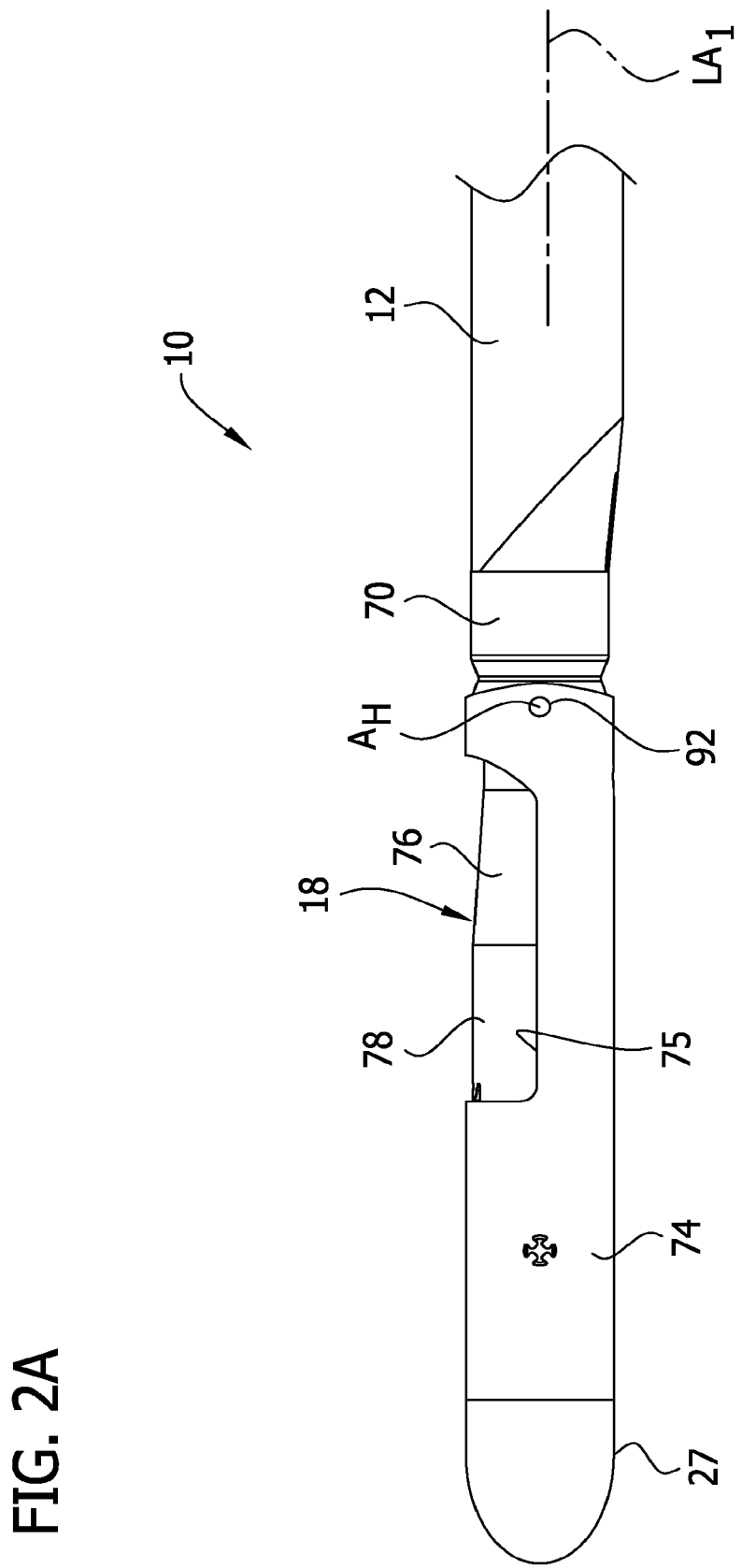
FIG. 2A is an enlarged fragmentary side elevation of a distal end portion of the tissue-removing catheter, with a cutter of the tissue-removing catheter in a non-deployed position.
Figure 2B:
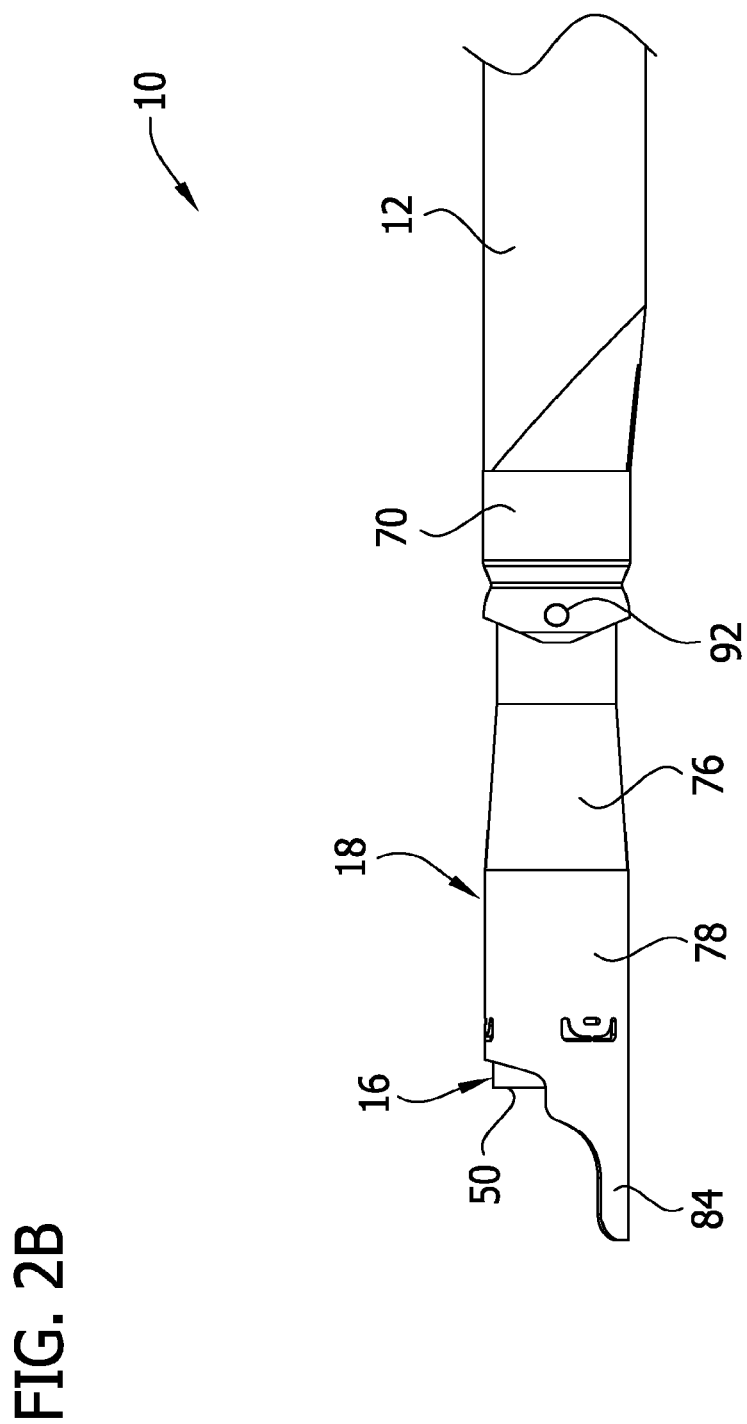
FIG. 2B is similar to FIG. 2A, except a cutter housing is removed to show hidden components.

The cutter housing 74 is hingedly attached to the deployment adaptor 70 at its proximal end via a hinge connector 92 (e.g., a hinge pin, a trunnion, a living hinge, or the like) on the deployment adaptor 70 (see FIGS. 2A, 4A, and 6A). The hinge connector 92 enables the cutter housing 74 to pivot (broadly, deflect) relative to the catheter body 12, the cutter adaptor 18, and the cutter generally transverse to the longitudinal axis $LA_1$ of the catheter body 12, for deploying and retracting the cutter 16, as shown in FIGS. 2-5. The distal tip 27 of the catheter 10 may be secured to the distal end of the cutter housing 74, so that the tip moves with the cutter housing.

To open the deployment mechanism 24, thereby deploying the cutter 16, the driveshaft 20 (and the screw conveyer 25) is moved proximally, such as by moving the lever 40 on the handle 32. As the driveshaft 20 is moved proximally, the opening ramp follower 90 in the cutter housing 74 runs along the exterior of the cutter adaptor 18 (more specifically, the exterior of the proximal tube piece 76) causing the cutter housing 74 to pivot (broadly, deflect) relative to the catheter body 12 and about the hinge axis. As the cutter housing 74 deflects, the cutting edge 50 of the cutter 16 extends through the cutter window 75 in cutter housing, whereby the cutting edge 50 is exposed outside the cutter housing. As shown in FIG. 4A, when the cutter 16 is in the deployed configuration, the longitudinal axis $LA_2$ of the cutter extends at an angle $\alpha_z$ offset from a central longitudinal axis $LA_4$ of the cutter housing 74. This offset angle $\alpha_2$ may measure from about 5 degrees to about 15 degrees. As seen in FIGS. 4A and 5, in the deployed position, only a circumferential portion of the cutting edge 50 (i.e., an exposed circumferential portion) extends through the window 75, while the remaining circumferential portion of the cutting edge does not extend through the window and is not exposed (i.e., a non-exposed circumferential portion). The ratio of the exposed circumferential portion to the non-exposed circumferential portion is the effective-exposure of the cutting edge 50. In the illustrated embodiment, less than half of the circumference of the cutting edge 50 is exposed, at any instant in time, as the cutter 16 is rotating, and therefore, the effective-exposure of the cutting edge is less than 50%.

To close the deployment mechanism, thereby retracting the cutter 16 in the stowed configuration (as shown in FIGS. 1-3), the driveshaft 20 (and the screw conveyer 25) is moved distally from its proximal position, such as by moving the lever 40 on the handle 32, which may also turn off the cutter driver 30 and stop rotation of the cutter 16, or the driveshaft may continue rotating. Moving the driveshaft 20 is distally, which moves the cutter 16 and hence the cutter adaptor 18 distally, causes the closing ramp follower 88 in the cutter housing 74 to move along the tongue 84 at the distal end of the cutter adaptor, thereby driving the cutter housing to pivot about the hinged axis $A_H$ toward the closed position. As the cutter housing 74 pivots toward the cutter 16, the cutting edge 50 reenters the cutter housing through the cutter window 75. When the cutter 16 is in its fully non-deployed position inside the cutter housing 74, the distal end of the tongue 84 is received in a tongue slot 98 (FIGS. 3 and 5) to inhibit pivoting of the cutter housing 74 about the hinge axis. When the driveshaft 20 is moved proximally, the tongue 84 withdraws from the tongue slot 98 to allow the cutter housing 74 to pivot about the hinge axis. The shape of the tongue 84 and closing ramp follower 88 allows the cutter housing 74 to first pivot (upon retraction of the cutter 16) and then allows the cutter to move axially into the cutter housing from the cutter window 75. The opposite happens when the cutter 16 is deployed. The cutter 16 first moves axially into the cutter window 75 and then the cutter housing 74 is pivoted to expose the cutting edge 50. It will be understood that the force for both deploying and retracting the cutter 16 is provided entirely by the user through movement of the cutter 16, cutter adaptor 18 and the drive shaft 20 (or the drive shaft and the screw blade 25).

In an exemplary operation, the catheter 10 is inserted into the body lumen (e.g., artery) so that the cutter 16 is positioned adjacent the target site. Fluoroscopy or other imaging techniques may be used to facilitate placement of the catheter 10 in the body lumen. During placement of the catheter 10 in the body lumen, the deployment mechanism 24 is closed and the cutter 16 is in the non-deployed position. At the target site, the deployment mechanism 24 is opened, such as by moving the lever 40 on the handle 32 proximally, to impart proximal movement of the driveshaft 20 relative to the catheter body 12 and the cutter housing 74, whereby the cutter adaptor 18 and the cutter 16 are also moved proximally relative to the cutter housing. As the cutter adaptor 18 moves proximally, the tongue 84 at the distal end of the cutter adaptor withdraws from the tongue slot 98 in the cutter housing 74, and opening ramp follower 90 in the cutter housing runs along the exterior surface of the proximal tube piece 76. Thus, the cutter adaptor 18, more specifically proximal tube piece 76, acts as a camming element for opening the deployment mechanism 24. As the proximal tube piece 76 rides along the opening ramp follower 90, the cutter housing 74 pivots relative to the cutter adaptor 18, the cutter 16, and the catheter body 12, about the hinge axis $A_H$, and a portion of the cutting edge 50 of the cutter extends through the cutter window 75 defined by the cutter housing. As explained above, an urging mechanism (not shown) may urge the cutting edge 50 toward the body lumen, and the offset cutter housing 74 may also facilitates urging of the cutter toward the body lumen.

In one example, deploying the cutter 16 using the lever 40 also actuates or turns on the cutter motor 30 to impart rotation of the driveshaft 20 and the cutter. Deployment of the cutter 16 using the lever 40 may also actuate or turn on the conveyor motor 66 to impart rotation of the screw blade 25, or alternatively, a separate actuator for turning on the conveyor motor may be provided on the handle. With the cutter 16 deployed and rotating, the catheter 10 is moved distally within the body lumen, and the rotating cutting edge 50 removes the tissue (e.g., plaque) from the body lumen (e.g., from an artery). As the tissue is being removed, the removed tissue moves through the annular cutting edge 50, into the axial cavity 52 in the cutter 16, and then passes into the eccentric opening 68. The removed tissue moves proximally within the cutter adaptor 18, where the thread 65*a* on the annular bearing member 65 and then the thread 69 on the rotating screw blade 25 pick up the removed tissue and transport the tissue proximally within the tissue-transport passage 23.

After completing a pass through the target site and removing a strip of tissue from the body lumen, the deployment mechanism 24 may be closed and the cutter motor 30 turned off (or alternatively, the motor may remain on) by moving the driveshaft 20 (and the screw conveyor 25) distally relative to the catheter body 12 using the lever 40 on the handle 32. As the driveshaft 20 is moved distally, the closing ramp follower 88 runs along the tongue 84 to drive pivoting of the cutter housing 74 relative to the cutter adaptor 18 and the cutter 16 about the hinge axis $A_H$. When the cutter 16 is in its fully non-deployed position inside the cutter housing 74 (as shown, for example, in FIGS. 1-3), the distal end of the tongue 84 is received in the tongue slot 98 in the cutter housing 74 and the cutting edge 50 is received in the cutter housing and unexposed. With the cutter motor 30 turned off (in one embodiment) and the cutter 16 in the non-deployed position, the catheter 10 is moved proximally within the body lumen to allow for another pass through the target site. In one embodiment, the conveyor motor 66 remains on after closing the deployment mechanism 24 and when the cutter motor 30 is off, so that the screw conveyor 25 continues to transport the removed tissue proximally within the catheter body 12. In one example, the handle 32 may include an actuator (e.g., a button or other device) to allow the practitioner to choose whether the conveyor motor 66 is to remain on when the cutter motor 30 is off. Thus, in such an example, the conveyor motor 66 and the screw conveyor 25 is selectively operable independently of the cutter motor 30 and the driveshaft 20. In one embodiment, the screw conveyor 25 may be rotated in a direction opposite that of the driveshaft 20 and the cutter 16. In another embodiment, the screw conveyor 25 may be rotated in the same direction as the driveshaft 20 and the cutter 16. In yet another embodiment, the handle 32 may include an actuator (not shown) for selecting the direction of rotation of the screw conveyor 25.

Referring now to FIGS. 10-18, a second embodiment of a tissue-removing catheter for removing tissue from a body lumen is generally indicated at 110. Briefly, the atherectomy catheter 110 includes an elongate tubular catheter body 112 having opposite proximal and distal ends, a central longitudinal axis $LA_5$ (FIG. 11A) extending between the distal and proximal ends. The catheter body 112 may be similar or substantially identical to the catheter body 12 of the first embodiment, and therefore, the disclosure set forth above with respect to the catheter body of the first embodiment is equally applicable to the catheter body of the second embodiment. A rotatable cutter, generally indicated at 116, is operatively connected to the distal end of the catheter body 112 for removing tissue from a body lumen. The catheter 110 also includes a hollow cutter driveshaft 120 (FIGS. 12 and 14), which drives rotation of the cutter 116, and a separate screw conveyor, generally indicated at 122 (also known as an auger conveyor), which transports or moves removed tissue proximally within the catheter body 12. The cutter driveshaft 120 defines an internal, tissue-transport passage 123 through which a screw blade 125 (or flighting) of the screw conveyor extends.

Figure 12:
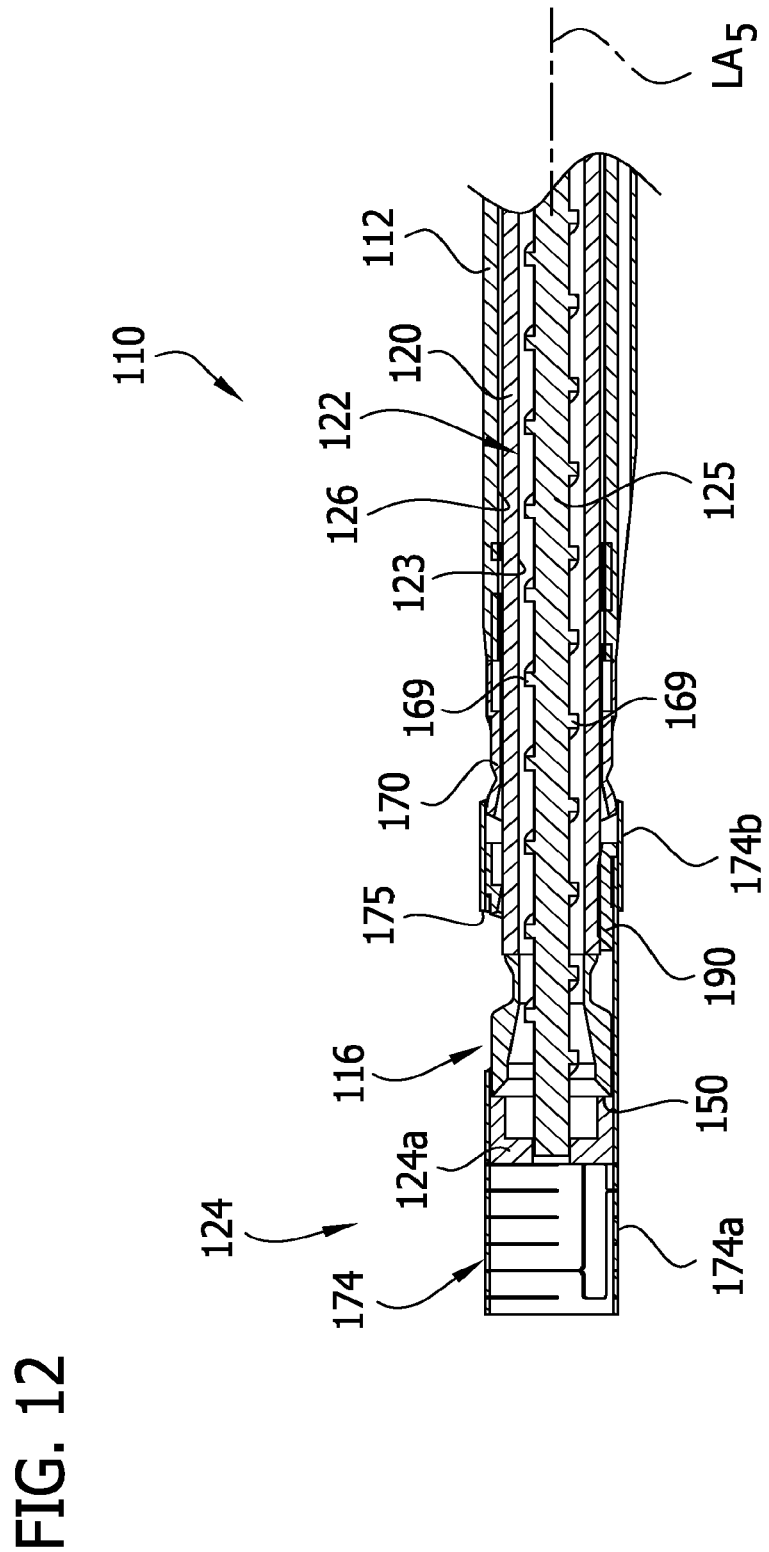
FIG. 12 is a longitudinal section of the distal end portion of the tissue-removing catheter of FIG. 11A.
Figure 14:
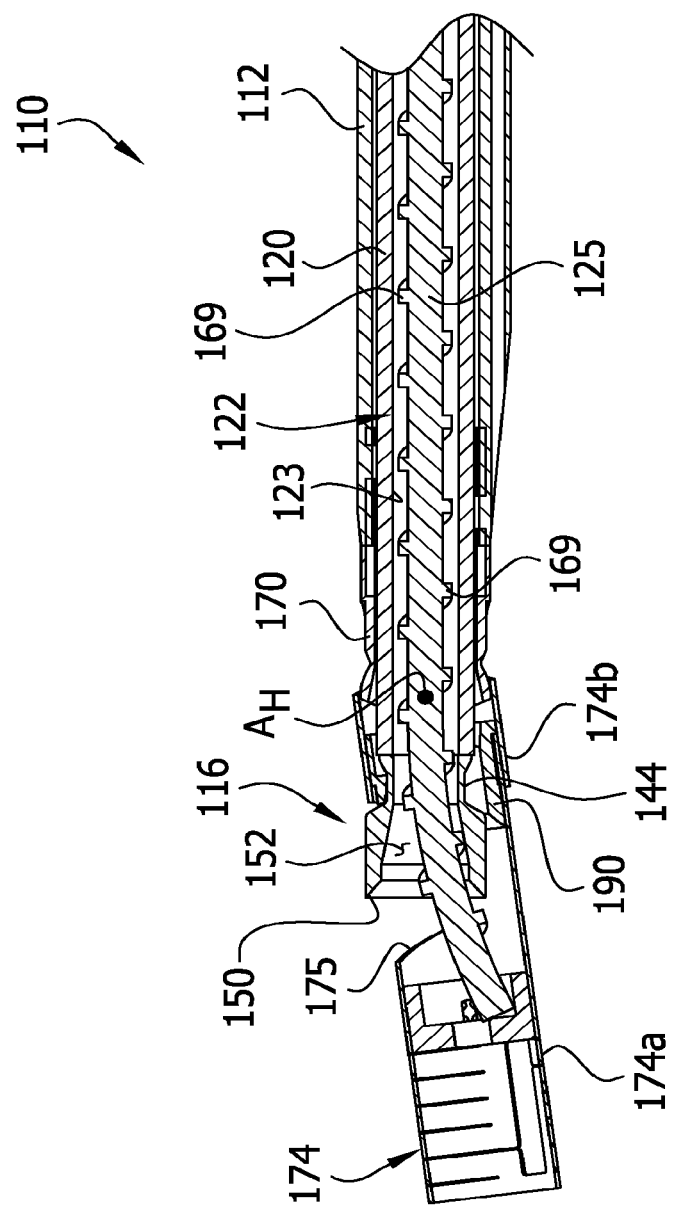
FIG. 14 is a longitudinal section of the distal end portion of the tissue-removing catheter of FIG. 13A.

Referring to FIGS. 12 and 14, as set forth above, the catheter 110 includes the rotatable cutter 116 and the driveshaft 120 for imparting rotation of the cutter. The driveshaft 120 extends along a longitudinal passage 126 in the catheter body 112 so that the driveshaft is generally coaxial with the catheter body. As explained below, in the illustrated embodiment the driveshaft 120 is rotatable about its axis independently of the screw blade 125, and the screw blade is rotatable about its axis independently of the driveshaft. A distal end portion of the driveshaft 120 is operatively connected to the rotatable cutter 116 for selectively driving rotation of the cutter generally about the longitudinal axis $LA_5$ of the catheter body 112. In the illustrated embodiment, the distal end portion of the driveshaft 120 is fixedly secured to the cutter 16. The shank of the driveshaft 120 is generally flexible and may be formed from one or more coils (e.g., stainless steel coil(s)), or a torque tube (e.g., a polyimide tube with a layer of braided stainless steel wire embedded therein). The shank of the driveshaft 120 may have a very high torsional stiffness and sufficient tensile strength, but is generally laterally flexible. Depending upon the desired torque transmission, diameter and flexibility, any of a variety of other materials and constructions may also be used.

Figure 10:
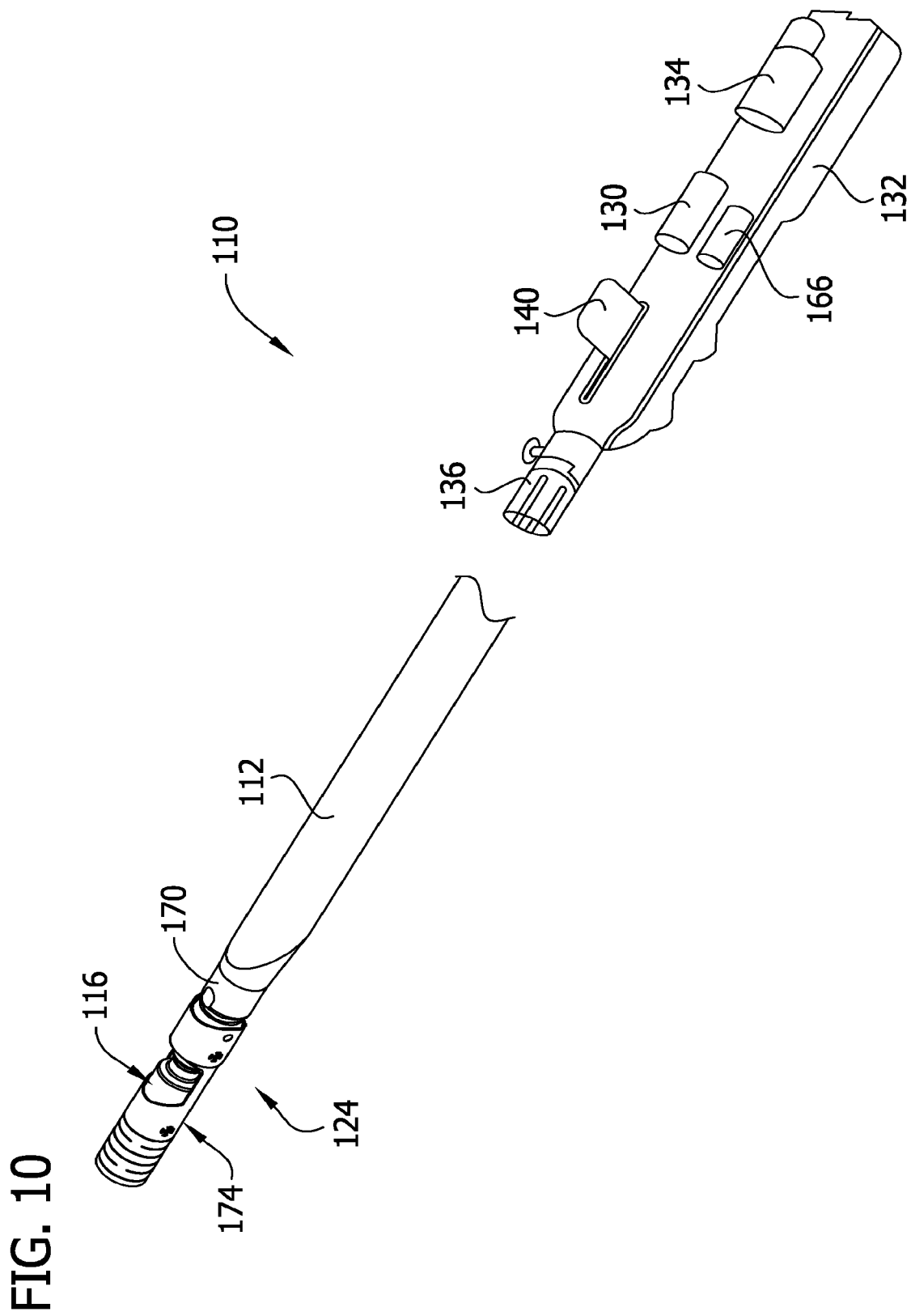
FIG. 10 is fragmentary perspective of a second embodiment of a tissue-removing catheter.

Referring to FIG. 10, the proximal end of the driveshaft 120 is operably connected to a cutter motor 130 (broadly, a cutter driver) to impart rotation of the driveshaft relative to catheter body 112. In one example, the cutter motor 130 is disposed within a handle 132 (shown with a cover removed in FIG. 10) that is releasably connectable to the proximal end of the catheter 110. The handle 132 may be similar or substantially identical to the handle 32 of the first embodiment. For example, in addition to the cutter motor 130, the handle 132 may house a power source 134 (e.g., batteries) for the cutter motor, a microswitch (not shown) for activating cutter motor, and a catheter connector 136 for connecting the motor to the proximal end portion of the driveshaft 120. In some embodiments, the cutter motor 130 can rotate the driveshaft 120 between 1,000 rpm and 10,000 rpm or more, if desired. As explained in more detail below, the handle 132 may include one or more input devices, such as lever 140, which controls the major operations of the catheter 110, such as axial movement of the driveshaft 120 to actuate a deployment mechanism 124, and rotation of the driveshaft 120 and the cutter 116 via the cutter driver 130. It is understood that the driveshaft 120 may be driven in other ways without departing from the scope of the present invention.

Figure 16:
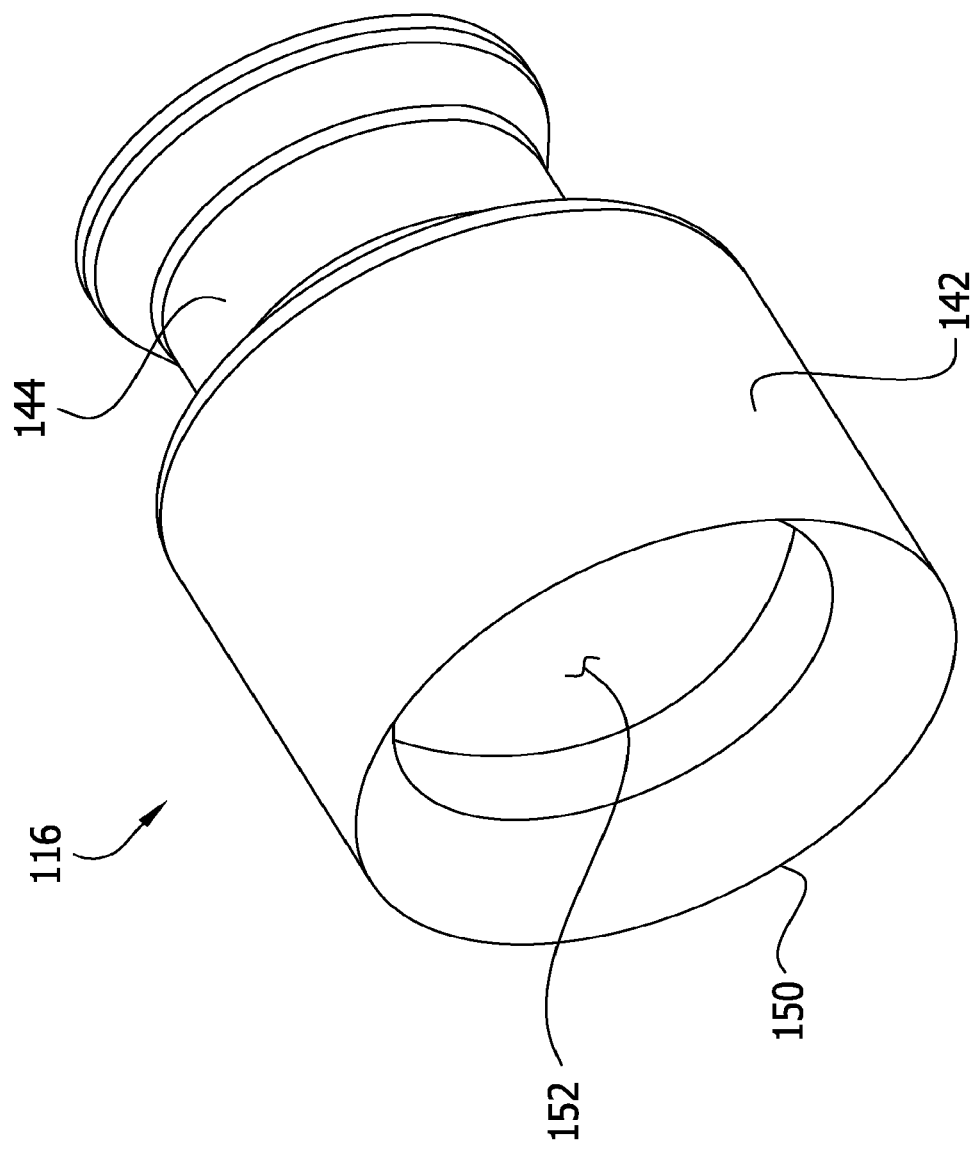
FIG. 16 is an enlarged, front perspective of the cutter of the tissue-removing catheter of FIG. 10.
Figure 17:
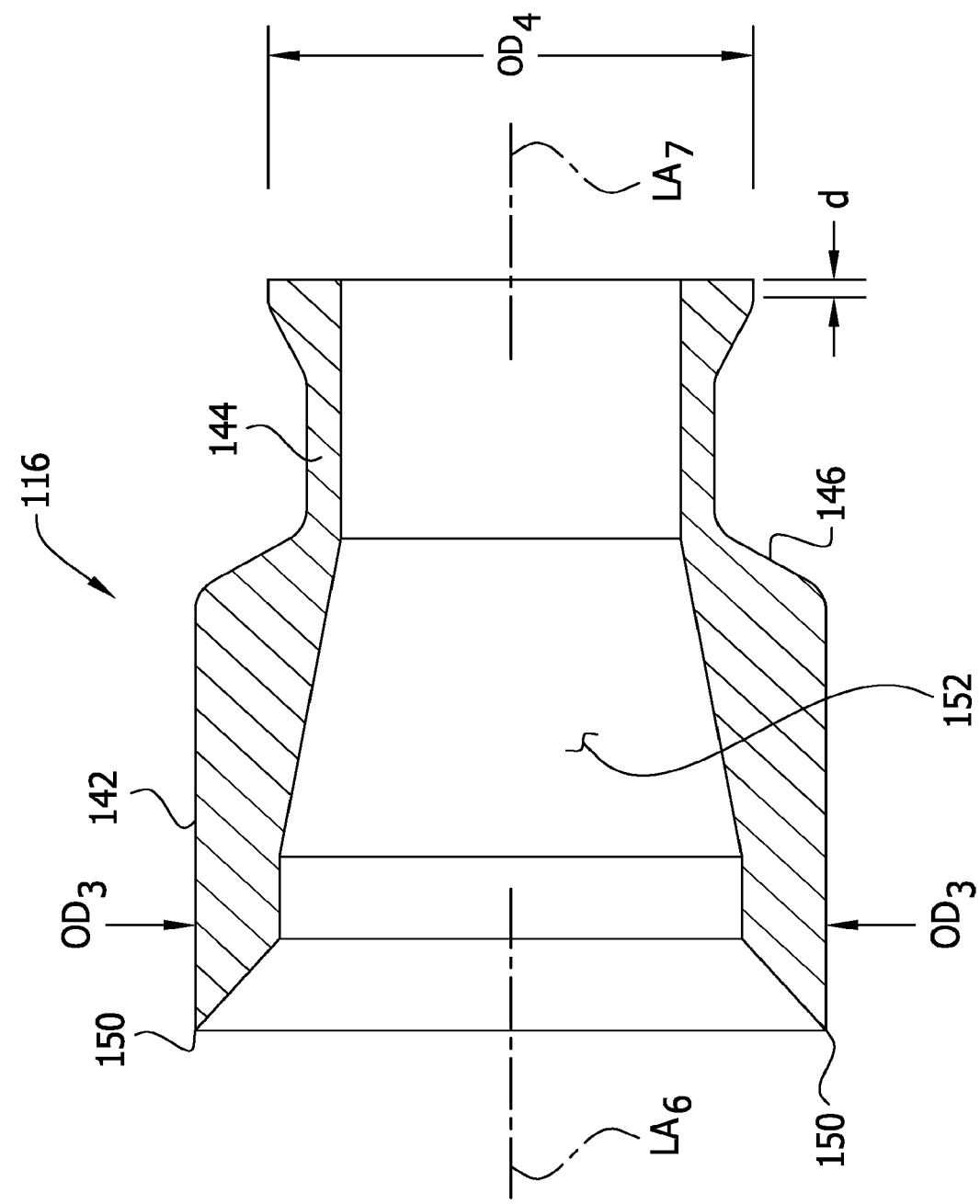
FIG. 17 is an enlarged, longitudinal section of the cutter of FIG. 16.
Figure 18:
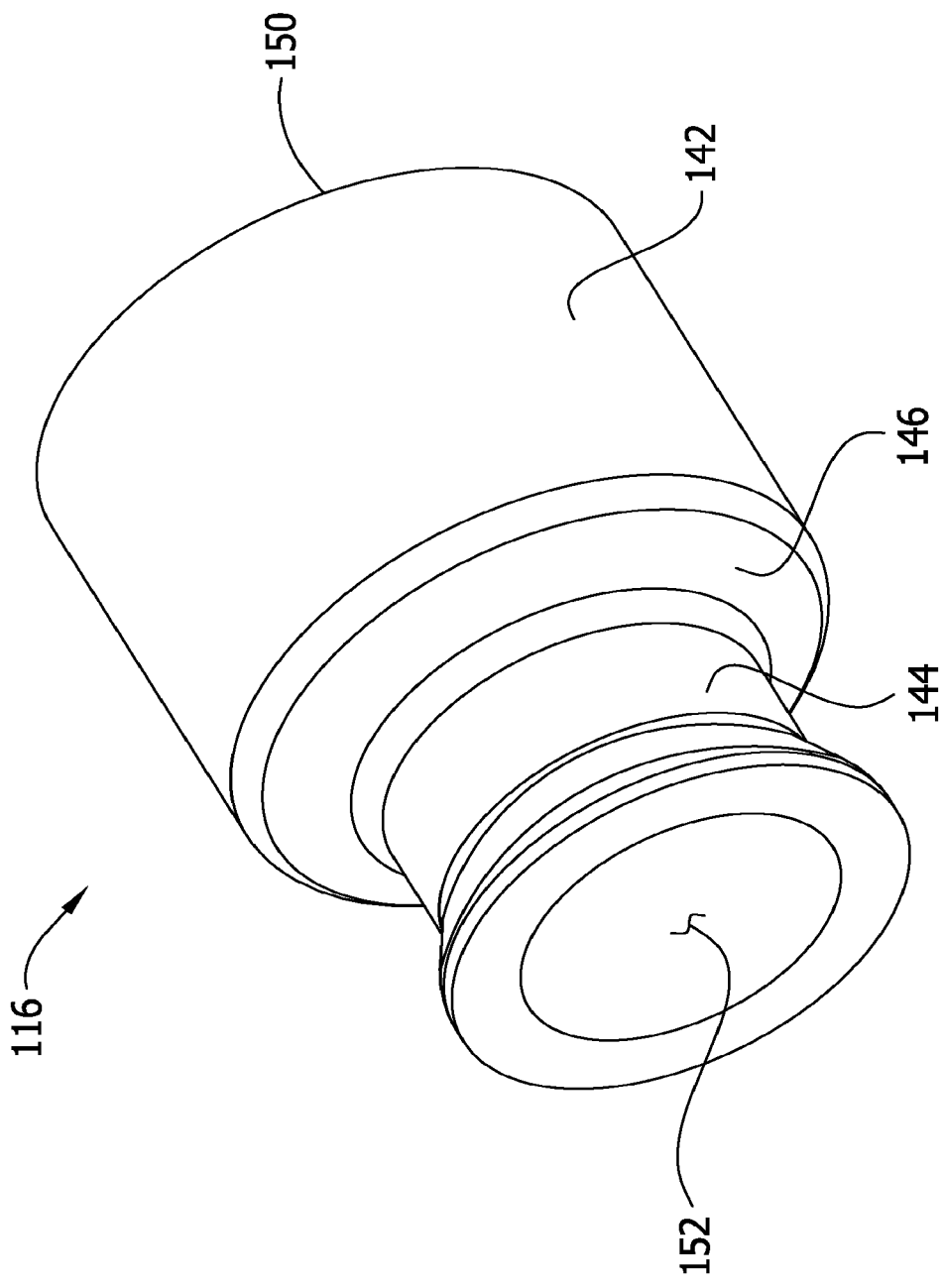
FIG. 18 is an enlarged, rear perspective of the cutter of FIG. 16.

As seen best in FIGS. 16-18, the rotatable cutter 116 has opposite proximal and distal ends and a longitudinal axis $LA_6$ (FIG. 17) extending therebetween. The cutter 116 has a generally cylindrical distal cutting portion 142, a proximal stem 144 (broadly, a driveshaft-connection portion), and a transitional portion 146 intermediate the distal cutting portion and the stem. The distal cutting portion 142 has an outer cross-sectional dimension $OD_3$ (e.g., an outer diameter) that is greater than an outer cross-sectional dimension $OD_4$ (e.g., an outer diameter) of the stem 144, and the exterior of the transitional portion 146 tapers (e.g., necks down) longitudinally from the distal cutting portion to the stem. The cutter 116 may be formed as a single, one-piece construction, or may be formed from separate components secured to one another in a suitable manner, such as welding, soldering, adhesives, mechanical interference fit, threaded engagement and the like. As a non-limiting example, the cutter 116 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Referring still to FIGS. 16-18, the distal cutting portion 142 of the cutter 116 includes an annular cutting edge 150 at the distal end thereof, and an axial, through cavity 152, defined by an interior surface of the cutter 116, extending from the cutting edge through the stem 144 of the cutter. In one non-limiting example, the annular cutting edge 150 is beveled from an exterior surface of the cutter toward the interior surface to define the sharp, distal cutting edge 150. The cutting edge 150 may be formed separately from the distal cutting portion 142 of the cutter 116 and attached thereto, or the cutting edge may be formed integrally with the distal cutting portion of cutter. In the embodiment illustrated in FIGS. 16-18, the annular cutting edge 150 has a generally smooth surface. In other embodiments, the annular cutting edge 150 may include one or more raised elements (e.g., breakers; not shown), such as disclosed above with respect to FIGS. 7-9, the teachings of which apply equally to the present embodiment. The cutting edge may be of other configurations without departing from the scope of the present invention.

The stem 144 connects the cutter 116 to the distal end of the driveshaft 120 so that rotation of the driveshaft imparts rotation of the cutter 116 about its longitudinal axis $LA_6$ (i.e., the rotational axis of the cutter is coincident with the central longitudinal axis of the cutter). In the illustrated embodiment, and as shown in FIG. 17, a central longitudinal axis $LA_7$ of the stem 144 is coincident with the central longitudinal axis $LA_6$ of the cutter 116. In the illustrated embodiment, the distal end of the driveshaft 120 abuts the stem 144 and is secured thereto, such as by soldering, welding, brazing, or in other ways. The axial cavity 152 defined by the cutter 116 extends generally axially through the proximal end of the cutter 116 and is in communication with the tissue-transport passage 123 defined by the driveshaft 120 and the screw blade 125 so that tissue removed by the cutter passes through the axial cavity and into the tissue-transport passage, where it is picked up and transported proximally by the screw blade 125, as explained in more detail below.

Referring to FIGS. 12 and 14, the screw blade 125 extends through the driveshaft 120 and the axial cavity 152 of the cutter 116. In one version (as shown in FIG. 12), distal end portion of the screw blade 125 is operably connected to the deployment mechanism 124 at a location distal of the cutter 116. In particular, the distal end portion of the screw blade 125 is connected to a bearing coupling 124a in a cutter housing 174 of the deployment mechanism 124 to support the distal end portion of the screw blade. The screw blade 125 rotates relative to the bearing coupling 124a. The distal end portion of the screw blade 125 may be connected to the catheter body 112 in other ways. In another version (as shown in FIG. 14), the distal end portion of the screw blade 125 is free from securement to the deployment mechanism 124.

The screw blade 125 includes a helical thread 169 on the exterior of its shank and extending longitudinally thereon so that rotation of the screw blade 125 about its axis moves removed tissue proximally within the tissue-transport passage 123 of the driveshaft 120. In the illustrated embodiment, the thread 169 is a right-handed thread (as viewed from the proximal end of the driveshaft screw blade 125), so that rotation of the screw blade clockwise (as viewed from the proximal end of the screw conveyor) relative to the tissue-transport passage 123 transports the tissue proximally. The tissue transport passage 123 and the screw conveyor thread 169 may extend back to the proximal end portion of the catheter body 112 and may empty into a tissue receptacle (not shown). The tissue transport passage 123 and screw conveyor thread 169 may stop short of the proximal end portion of the catheter body 112. The thread 169 may be formed on the shank of the screw blade 125 in a suitable manner.

In one example, the cross-sectional dimension (e.g., inner diameter) of the tissue-transport passage 123 is slightly greater than the major diameter of the exterior thread 169 on the screw blade 125 so that there is a small radial gap (or play) between the thread on the screw blade and interior surface of the driveshaft 120 defining the tissue-transport passage 123. In this example, the radial gap is such so as not to inhibit or impede rotation and axial movement of the screw blade 125 in tissue-transport passage 123, and at the same time, substantially inhibit tissue from passing between the thread 169 on the screw blade and the interior surface of the driveshaft 120 defining the tissue-transport passage. For example, the diameter of the tissue-transport passage 123 may be from about 0.001 in (0.025 mm) to about 0.005 in (0.127 mm) greater than the major diameter of the exterior thread 169. In another embodiment, the radial gap between the thread 169 on the screw blade 125 and interior surface of driveshaft 120 defining the tissue-transport passage 123 is so that removed tissue is pinched between the thread and the interior surface, without substantially macerating the tissue, to facilitate proximal movement of the tissue intact. For this embodiment, the radial gap may measure from greater than about 0.005 in (0.127 mm) to about 0.020 in (0.508 mm), and in one example, from about 0.010 in (0.245 mm) to about 0.015 in (0.381 mm). It is understood that in some embodiments the screw conveyor 122 may be omitted without departing from the scope of the present invention.

Referring to FIG. 10, the proximal end of the screw blade 125 is operably connected to a conveyor motor 166 (broadly, a conveyor driver) to impart rotation of the screw blade 125 relative to catheter body 112. In one example, the conveyor motor 166 is disposed within the handle 132 (shown with a cover removed in FIG. 10) that is releasably connectable to the proximal end of the catheter 110. The power source 134 (e.g., batteries) may power the conveyor motor 166, in addition to the cutter motor 130, or a different power source may be provided. A different microswitch (not shown) may be used to activate the conveyor motor 166. The lever 140 may control rotation of the screw blade 125 via the conveyor motor 166, or a different actuator may be provided to activate the conveyor motor. In the illustrated embodiment, the cutter driveshaft 120 is axially moveable relative to the screw blade 125, and the screw blade may be fixed axially relative to the catheter body 112. As such, the lever 140 does not impart axial movement of the screw blade 125 relative to the catheter body 112. As explained below, in one embodiment, the conveyor motor 166 is operable independently of the cutter motor 130 to allow for transportation of removed tissue even if the cutter 116 is not in operation. The lever 140 may still be configured to operate the conveyor motor 166 independently of the cutter motor 30, or the handle 132 may include a separate input device (e.g., a button or other actuator) for operating the conveyor motor independently of the cutter motor. It is understood that the screw blade 125 may be driven in other ways without departing from the scope of the present invention.

As set forth above, the tissue removed from the blood vessel by the cutting edge 150 passes proximally through the cutter 116, toward the tissue-transport passage 123 of the cutter driveshaft 130. In the illustrated embodiment, the screw blade 125 picks up removed tissue within the axial cavity 152 in the cutter 116 because the screw blade and the screw blade thread 169 extend through the cutter to a distal location. Thus, as can be seen from FIG. 14, as the tissue is being removed, it enters the axial cavity 152 in the cutter 116, where it is picked up by the screw blade 125, and transported proximally through the stem 144 of the cutter and into the tissue-transport passage 123, where it continues to be transported proximally by the screw blade. It is understood that the screw blade 125 may be of other configurations in other embodiments of the catheter without departing from the scope of the present invention. For example, the screw blade 125 may not pass distally through the axial cavity 152 of the cutter 116, but instead, the distal end of the screw blade may be located proximal of the cutter and/or the cutting edge 150 of the cutter. Moreover, a distal portion of the screw blade 125 may be free from the thread 169, so that the thread begins within the stem of the cutter, for example, or within the tissue-transport passage 123.

Figure 13B:
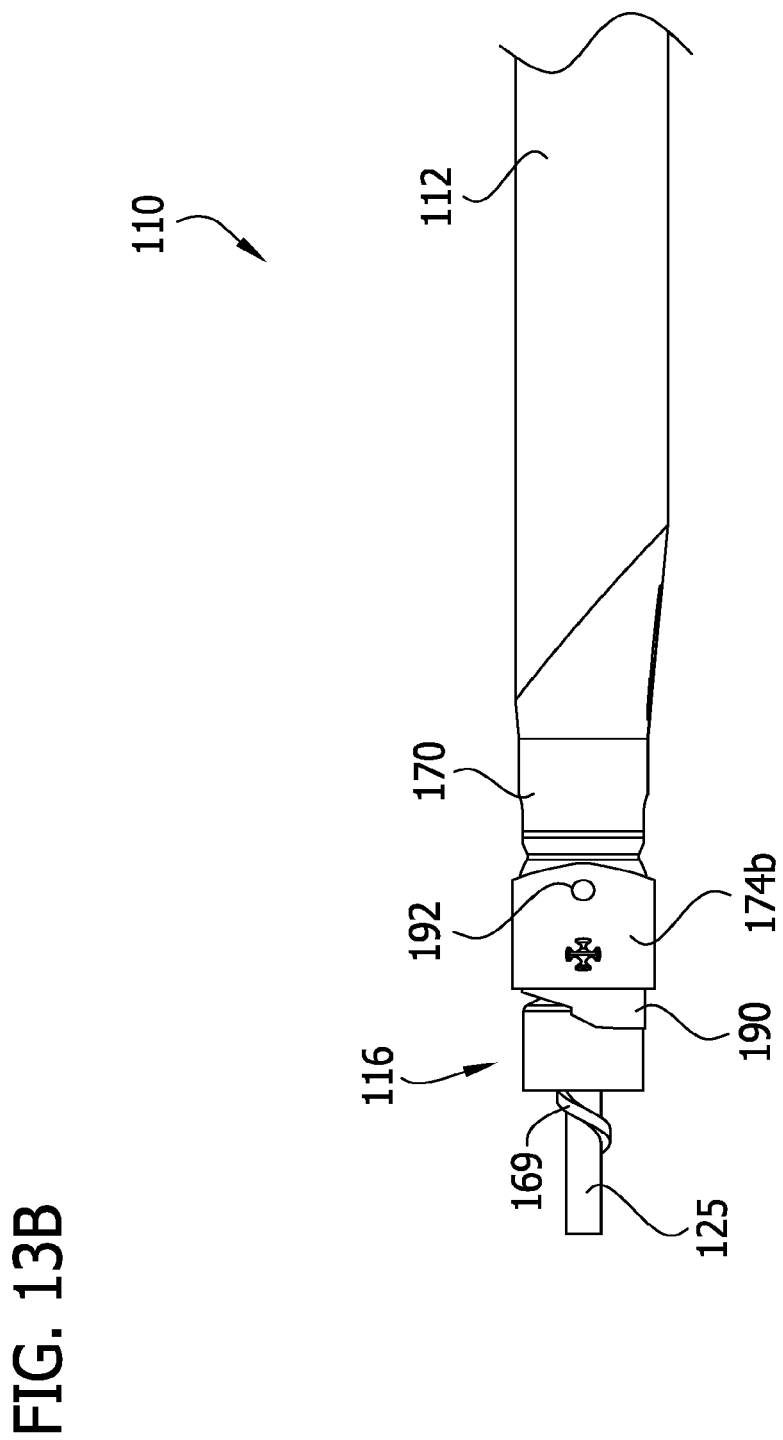
FIG. 13B is similar to FIG. 13A, except the cutter housing is removed to show hidden components.

As set forth above, the catheter 110 includes the deployment mechanism 124 for configuring the cutter 116 between the non-deployed position (FIGS. 11A and 12) and the deployed position (FIGS. 13A and 14). The deployment mechanism 124 is connected to a deployment adaptor 170 at the distal end of the catheter body 112. For purposes of the disclosure, the deployment adaptor 170 is considered part of the catheter body 112, and in particular, part of the distal end of the catheter body. In the illustrated embodiment, the deployment mechanism 124 includes a cutter housing, generally indicated at 174, including a distal housing piece 174a defining a cutter window 175, and a proximal housing piece 174b hingedly attached to the deployment adaptor 170 at the distal end portion of the catheter body 112. In the illustrated embodiment, the outer diameter of the distal housing piece 174a is smaller than the inner diameter of the proximal housing piece 174b. The outer diameter of the distal housing piece 174a may be minimized to facilitate insertion of the catheter, while the inner diameter of the proximal housing piece 174b may be maximized to increase the area through which removed tissue can pass proximally. The proximal housing piece 174b is hingedly attached to the deployment adaptor 170 at its proximal end via a hinge connector 192 (e.g., a hinge pin, a trunnion, a living hinge, or the like) on the deployment adaptor 170 (see FIG. 13A). As explained below, the hinge connector 192 enables the cutter housing 174 to pivot (broadly, deflect) relative to the catheter body 112 and the cutter generally transverse to the longitudinal axis $LA_5$ of the catheter body 112, for deploying and retracting the cutter 116, as shown in FIGS. 12 and 14. A tip (not shown) of the catheter 10, similar to tip 27, may be secured to the distal end of the cutter housing 174, so that the tip moves with the cutter housing. The cutter housing 174 may be generally rigid, specifically, more rigid than the catheter body 112.

Figure 11A:
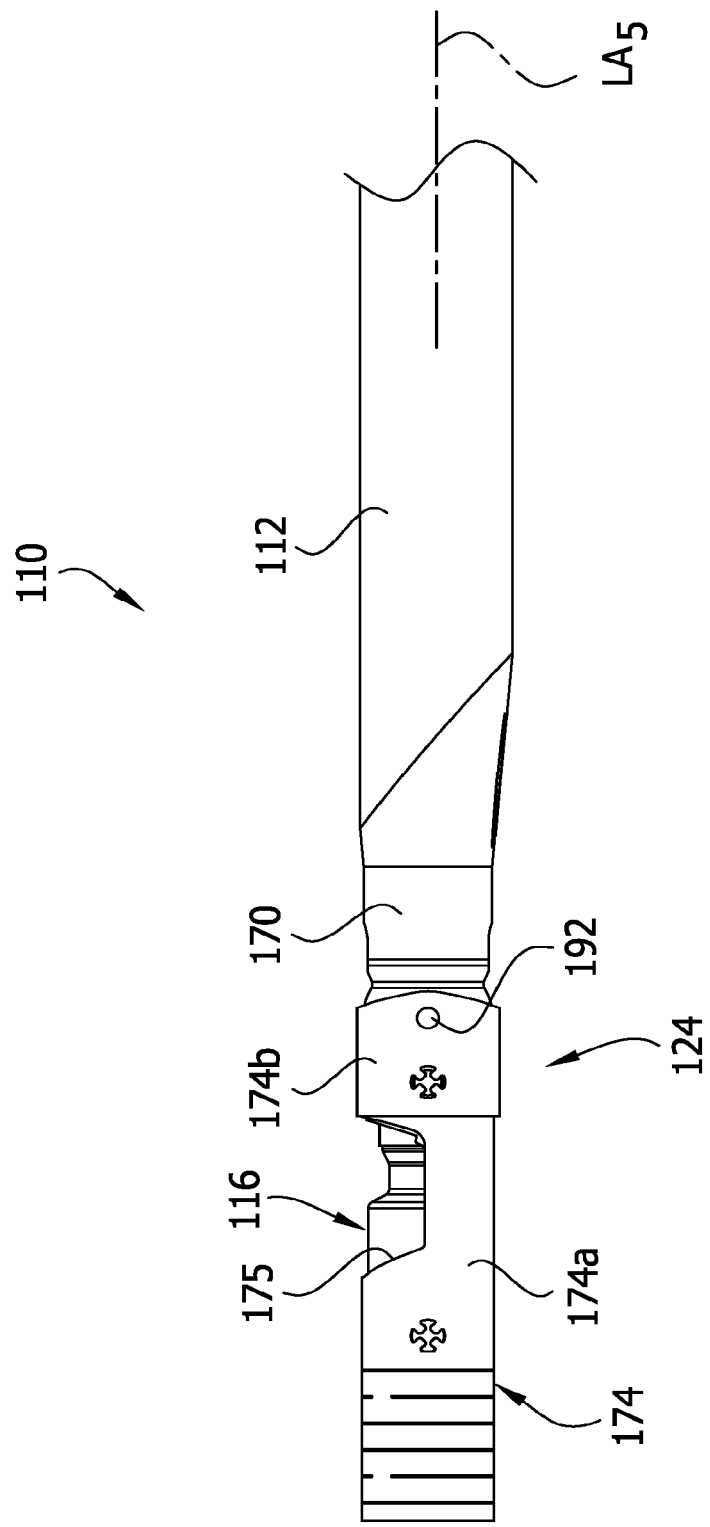
FIG. 11A is an enlarged fragmentary side elevation of a distal end portion of the tissue-removing catheter of FIG. 10, with a cutter of the tissue-removing catheter in a non-deployed position.
Figure 11B:
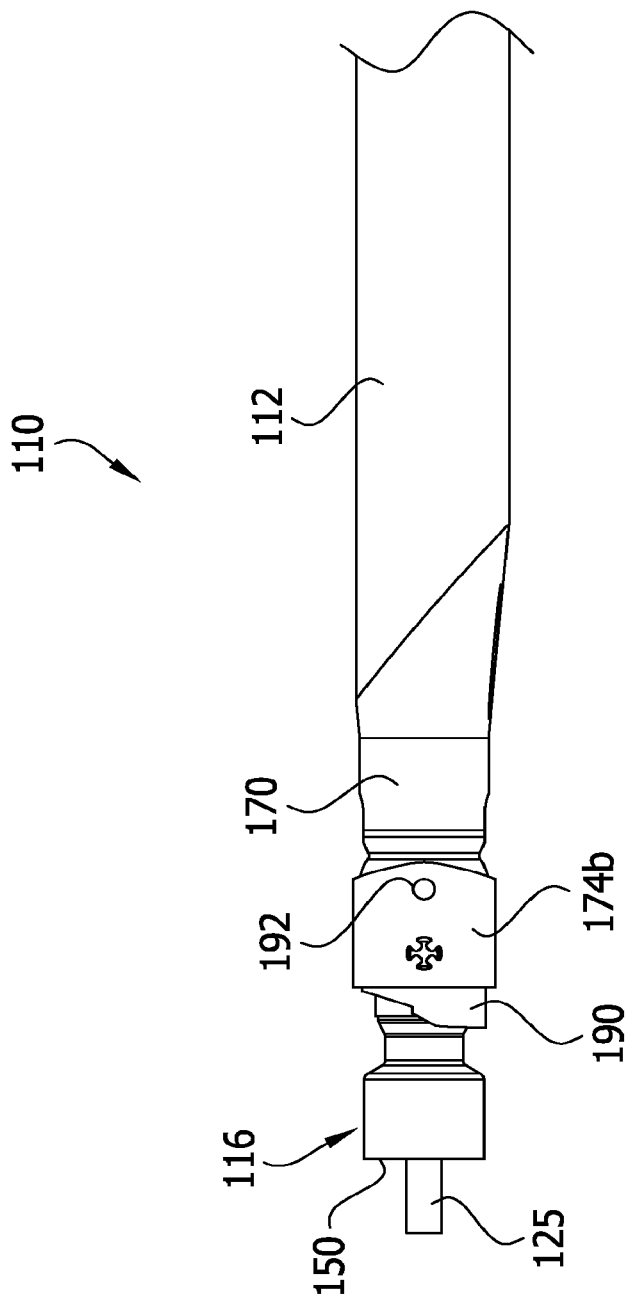
FIG. 11B is similar to FIG. 11A, except a cutter housing is removed to show hidden components.

The cutter 116 is axially (i.e., proximally and distally) moveable relative to the cutter housing 174, whereby proximal movement of the cutter drives the cutter housing to pivot about its hinge axis $A_H$ to open the deployment mechanism 124 and expose the cutting edge 150 through the cutter window 175 (FIGS. 13A and 14), and distal movement of the cutter drives the cutter housing to pivot about its hinge axis to close the deployment mechanism so that cutting edge is received in the cutter housing (FIGS. 11A and 12). The cutter 116 is axially moveable relative to the cutter housing 174 (and the catheter body 112) by axially moving the driveshaft 120, which imparts axial movement to the cutter 116. Accordingly, the cutter 116 moves conjointly with the driveshaft 120. In one embodiment, the driveshaft 120 is axially moveable relative to the catheter body 112 by actuating the lever 140 on the handle 132, which may also actuate the motor 130 to drive rotation of the driveshaft and the cutter 116. It has been found that in one embodiment, it is advantageous to have the entirety of the cutter 116 located distal of the hinge axis $A_H$ when the cutter is in its deployed position, as seen in FIG. 14. Should the stem 144 of the cutter 116 be located proximal of the hinge axis $A_H$ in its deployed position, it has been found that large stresses are placed on the welded or brazed joint between the stem and the driveshaft 120, which may lead to failure of the joint during rotation of the driveshaft. It is believed that when the entire cutter 116 is distal of the hinge axis $A_H$ when it is deployed, the more rigid catheter body 174 reduces the stresses on the joint. In one embodiment (FIG. 17), a proximal portion of the cutter 116 may have a length d of less than or equal to about 0.005 in (0.127 mm) so that the entire cutter 116 is proximal of the hinge axis $A_H$.

To open the deployment mechanism 124, thereby deploying the cutter 116, the driveshaft 120 is moved proximally, such as by moving the lever 140 on the handle 132. As the driveshaft 120 is moved proximally, a ramp follower 190 in the cutter housing 174 runs along the exterior of the cutter 116, causing the cutter housing 174 to pivot (broadly, deflect) relative to the catheter body 112 and about the hinge axis. As the cutter housing 174 deflects, the cutting edge 150 of the cutter 116 extends through the cutter window 175 in cutter housing, whereby the cutting edge is exposed outside the cutter housing. As shown in FIG. 13A, when the cutter 116 is in the deployed configuration, the longitudinal axis $LA_5$ of the cutter extends at an angle $\alpha_3$ offset from a central longitudinal axis $LA_3$ of the cutter housing 174. This offset angle $\alpha_3$ may measure from about 5 degrees to about 15 degrees. As seen in FIGS. 13A and 14, in the deployed position, only a circumferential portion of the cutting edge 150 (i.e., an exposed circumferential portion) extends through the window 175, while the remaining circumferential portion of the cutting edge does not extend through the window and is not exposed (i.e., a non-exposed circumferential portion). The ratio of the exposed circumferential portion to the non-exposed circumferential portion is the effective-exposure of the cutting edge 150. In the illustrated embodiment, less than half of the circumference of the cutting edge 150 is exposed, at any instantaneous time, as the cutter 116 is rotating, and therefore, the effective-exposure of the cutting edge is less than 50%.

To close the deployment mechanism 124, thereby retracting the cutter 116 in the stowed configuration (as shown in FIGS. 11A and 12), the driveshaft 120 is moved distally from its proximal position, such as by moving the lever 140 on the handle 132, which may also turn off the cutter driver 130 and stop rotation of the cutter 116, although the conveyor motor 166 may remain on in some embodiments. As the driveshaft 120 is moved distally, which moves the cutter 116 distally, the ramp follower 190 in the cutter housing 174 runs along the cutter 116, thereby driving the cutter housing to pivot about the hinged axis toward the closed position. As the cutter housing 174 pivots toward the cutter 116, the cutting edge 150 reenters the cutter housing through the cutter window 175. It will be understood that the force for both deploying and retracting the cutter 116 is provided entirely by the user through movement of the cutter 116 via the drive shaft 120.

In an exemplary operation, the catheter 110 is inserted into the body lumen (e.g., artery) so that the cutter 116 is positioned adjacent the target site. Fluoroscopy or other imaging techniques may be used to facilitate placement of the catheter 110 in the body lumen. During placement of the catheter 110 in the body lumen, the deployment mechanism 124 is closed and the cutter 116 is in the stowed position. At the target site, the deployment mechanism 124 is opened, such as by moving the lever 140 on the handle 132 proximally, to impart proximal movement of the driveshaft 120 relative to the catheter body 112 and the cutter housing 174, whereby the cutter 116 is also moved proximally relative to the cutter housing. As the cutter 116 moves proximally, the ramp follower 190 in the cutter housing runs along the exterior surface of the cutter. Thus, the cutter 116 acts as a caroming element for opening the deployment mechanism 124. As the cutter 116 rides along the ramp follower 190, the cutter housing 174 pivots relative to the cutter and the catheter body 112, about the hinge axis $A_H$, and a portion of the cutting edge 150 of the cutter extends through the cutter window 175 defined by the cutter housing. An urging mechanism (not shown) may urge the cutting edge 150 toward the wall of the body lumen, and the offset cutter housing 174 may also facilitates urging of the cutter 116 toward the wall of the body lumen.

In one example, deploying the cutter 116 using the lever 140 also actuates or turns on the cutter motor 130 to impart rotation of the driveshaft 120 and the cutter. Deployment of the cutter 116 using the lever 140 may also actuate or turn on the conveyor motor 166 to impart rotation of the screw blade 125. With the cutter 116 deployed and rotating, the catheter 110 is moved distally within the body lumen, and the rotating cutting edge 150 removes the tissue (e.g., plaque) from the body lumen (e.g., from a blood vessel). As the tissue is being removed, the removed tissue moves into the tissue passage 152 in the cutter 116, where the thread 169 on the rotating screw blade 125 moves the removed tissue proximally through the tissue passage and into the tissue-transport passage 123 in the driveshaft 120. The screw blade 125 continues to move the removed tissue proximally within the tissue-transport passage 123.

After completing a pass through the target site and removing a strip of tissue from the body lumen, the deployment mechanism 124 may be closed and the cutter motor 130 turned off (or alternatively, the motor may remain on) by moving the driveshaft 120 distally relative to the catheter body 112 using the lever 140 on the handle 132. Moving the driveshaft 120 is distally causes the ramp follower 190 to move along the cutter 116 to drive pivoting of the cutter housing 174 relative to the cutter about the hinge axis $A_R$. When the cutter 116 is in its fully non-deployed position inside the cutter housing 174 (as shown, for example, in FIGS. 11A and 12), the cutting edge 150 is received in the cutter housing and unexposed. With the cutter motor 130 turned off (in one embodiment) and the cutter 116 in the non-deployed position, the catheter 110 is moved proximally within the body lumen to allow for another pass through the target site. In one embodiment, the conveyor motor 166 remains on after closing the deployment mechanism 124 and when the cutter motor 130 is off, so that the screw conveyor 122 continues to transport the removed tissue proximally within the driveshaft 120. In one example, the handle 132 may include an actuator (e.g., a button or other device) to allow the practitioner to choose whether the conveyor motor 166 is to remain on when the cutter motor 130 is off. Thus, the conveyor motor 166 and the screw conveyor 122 are selectively operable independently of the cutter motor 130 and the driveshaft 120.

Comparing the first tissue-removing catheter 10 to the second tissue-removing catheter 110, it was determined where the outer diameters of the respective catheter bodies 12, 112, are equal, the cross-sectional area of the tissue-transport passage 23 of the first catheter may be greater than the cross-sectional area of the tissue-transport passage 123 of the second catheter. This is due to the fact that the screw blade 125 of the second catheter 110 is sized and shaped to extend through the cutter driveshaft 120, while the screw blade 25 of the first catheter 10 extends through the larger passage in the catheter body 12. In one example, the cross-sectional area of the tissue-transport passage 23 of the first catheter 10 (as calculated by the difference between the outer cross-sectional area of the screw blade 25 and the inner cross-sectional area of the catheter body 23) may be about 0.001385 in$^2$ (0.8935466 mm$^2$) while the cross-sectional area of the tissue-transport passage 123 of the second catheter 110 (as calculated by the difference between the outer cross-sectional area of the screw blade 125 and the inner cross-sectional area of the hollow driveshaft 120) may be about 0.000792 in$^2$ (0.51096672 mm$^2$).

Figure 20A:
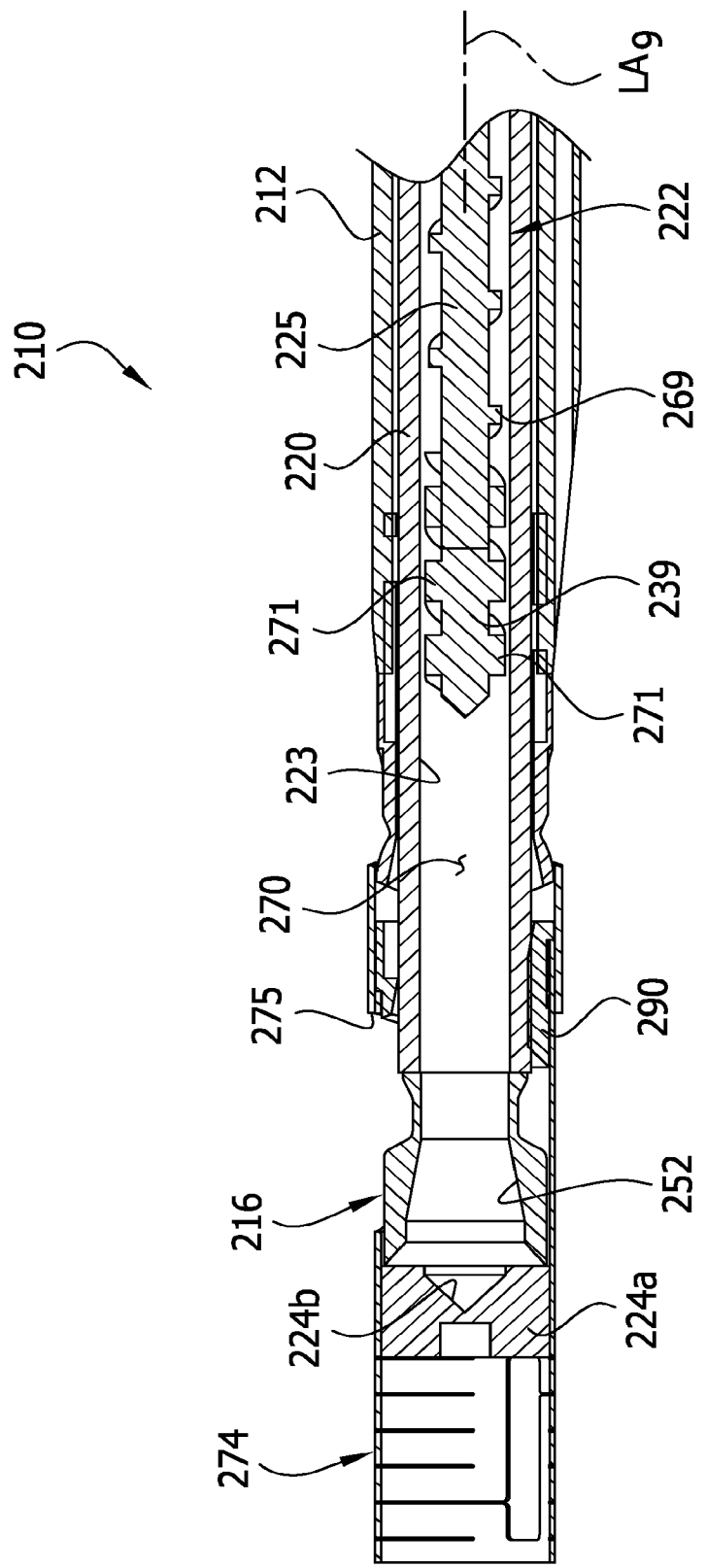
FIG. 20A is an enlarged fragmentary longitudinal section of a distal end portion of the tissue-removing catheter of FIG. 19, with a cutter in a non-deployed position and a screw blade in a proximal, tissue-collecting position.
Figure 20B:
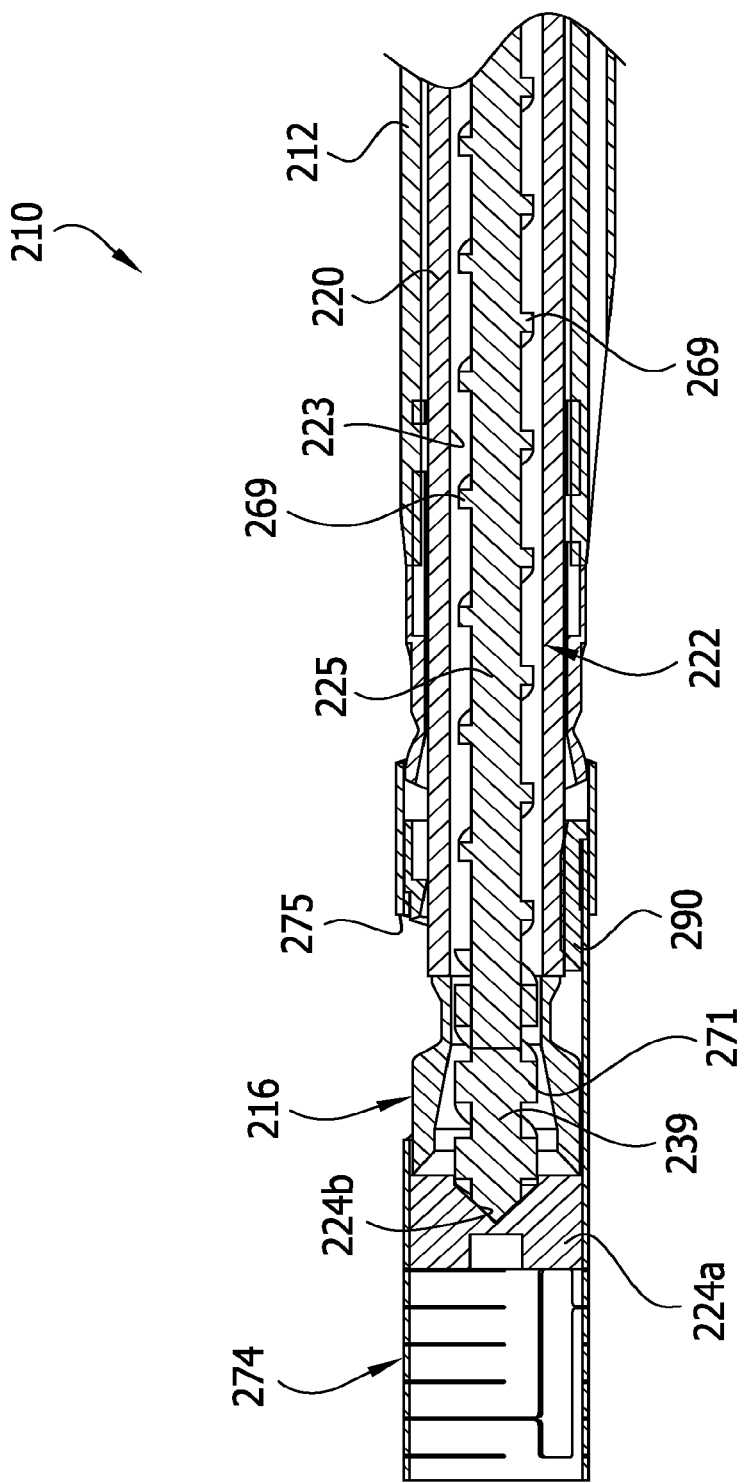
FIG. 20B is similar to FIG. 20A, with the cutter in the non-deployed position and the screw blade in a distal, tissue-conveying position.
Figure 20C:
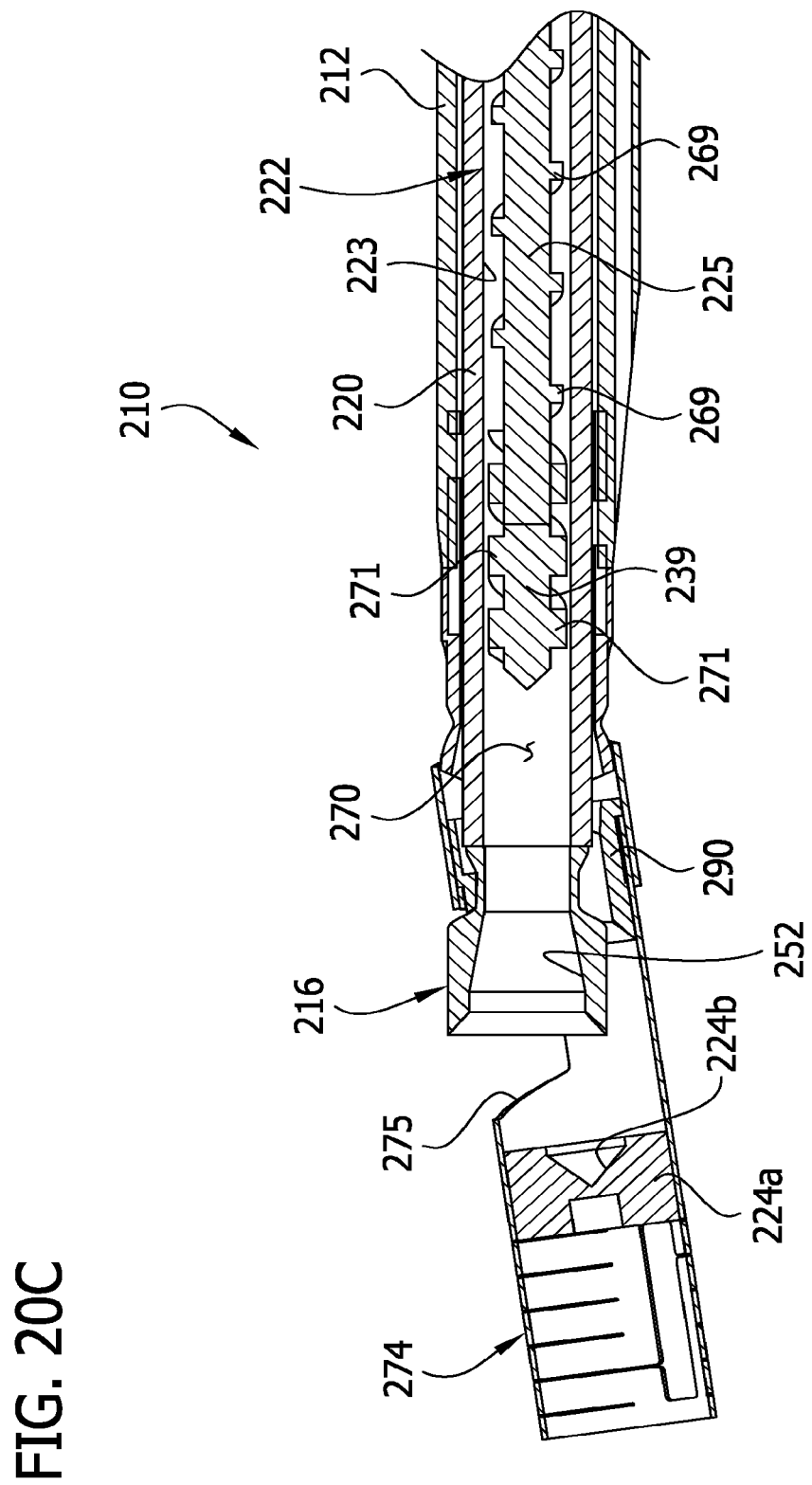
FIG. 20C is similar to FIG. 20A, with the cutter in a deployed, cutting position and the screw blade in the proximal, tissue-collecting position.

Referring to FIGS. 19-20C, a third embodiment of a tissue-removing catheter for removing tissue from a body lumen is generally indicated at 210. This catheter 210 is similar to the second embodiment of the tissue-removing catheter illustrated in FIGS. 10-18. Briefly, the atherectomy catheter 210 includes an elongate tubular catheter body 212 having opposite proximal and distal ends, a central longitudinal axis $LA_9$ (FIG. 20A) extending between the distal and proximal ends. The catheter body 212 may be similar or substantially identical to the catheter body 12 of the first embodiment, and therefore, the disclosure set forth above with respect to the catheter body of the first embodiment is equally applicable to the catheter body of the present embodiment.

A rotatable cutter, generally indicated at 216, is operatively connected to a hollow cutter driveshaft 220 for driving rotation of the cutter 216. The cutter 216 and the cutter driveshaft 220 may be similar or substantially identical to the cutter 116 and driveshaft 120 of the second embodiment, and therefore, the disclosure set forth above with respect to the cutter 116 and driveshaft 120 of the second embodiment is equally applicable to the cutter 216 and driveshaft 220 of the present embodiment. Moreover, the cutter driveshaft 220 is operably connected to a cutter motor 230 in a handle 232. The cutter motor 230 is powered by the power source 234. The cutter driveshaft 220 is movable axially within the catheter body 212 through use of lever 240, which may also activate the cutter motor 230 when the lever is moved distally, as set forth above with respect to the second embodiment of the catheter. The teachings set forth above with respect to the cutter motor 230, the lever 240, and the power source 234 are equally applicable to the catheter 210 of the present embodiment.

A deployment mechanism 224—including a two piece cutter housing 274 with a window 275, and an opening ramp 290—for exposing and retracting the cutter 216 may also be similar or substantially identical to the deployment mechanism 124 of the second embodiment, and therefore, the disclosure set forth above with respect to the deployment mechanism 124 of the second embodiment is equally applicable to the deployment mechanism 224 of the present embodiment.

Referring to FIGS. 20A-20C, a screw conveyor, generally indicated at 222, includes a screw blade 225 received in a tissue-transport passage 223 of the driveshaft 220. The screw blade 225 includes a helical thread 269, and in the illustrated embodiment, the screw blade has a boring bit 239 disposed on the distal end of the shank. The boring bit 239 includes a conical, distal tip and a helical, external thread 271. The boring bit 239 may be of other configurations. The screw blade 225 is rotatable about its axis, and as explained below, the screw blade is movable axially relative to the driveshaft 220 within the tissue-transport passage 223. Referring to FIG. 19, the proximal end of the screw blade 225 is operably connected to a conveyor motor 266 (broadly, a conveyor driver) to impart rotation of the screw blade 225 relative to catheter body 212. In one example, the conveyor motor 266 is disposed within the handle 232 (shown with a cover removed in FIG. 19) that is releasably connectable to the proximal end of the catheter 210. A power source 234 (e.g., batteries) for the cutter driveshaft 220 may also power the conveyor motor 266, or a different power source may be provided. A different microswitch (not shown) may be used to activate the conveyor motor 266. A lever 241 may control axial movement of the screw blade 225 relative to the driveshaft 220 and rotation of the screw blade 225 via the conveyor motor 266. As explained below, in one embodiment, the conveyor motor 266 is operable independently of the cutter motor 230 to allow for transportation of removed tissue even if the cutter 216 is not in operation. The lever 241 may be configured to operate the conveyor motor 266 independently of the cutter motor 230. It is understood that the screw blade 225 may be driven in other ways without departing from the scope of the present invention.

In an exemplary operation, the screw blade 225 is axially movable between a proximal, tissue-collection position (e.g., proximal of the cutter 216), as shown in FIGS. 20A and 20C, and a distal, tissue-conveying position (e.g., positioned within or distal of the cutter), as shown in FIG. 20B. The screw blade 225 is positioned in the proximal, tissue-collection position during the cutting operation when the cutter 216 is deployed (FIG. 20C) to define a tissue collection chamber 270 for receiving removed tissue. The screw blade 225 is also positioned in the proximal, tissue-collection position when the cutter 216 is in the non-deployed position (FIG. 20A) and before the screw blade is moved to its distal, tissue-conveying position. The tissue collection chamber 270 may be defined by the axial cavity 252 in the cutter 216 and a distal portion of the tissue-transport passage 223 in the cutter driveshaft 220. The removed tissue collects in the tissue collection chamber 270 during the cutting operation (FIG. 20C). After making a cutting pass through the lesion site, the cutter 216 is moved distally, such as by moving the lever 240 distally, to close the deployment mechanism 224 (FIG. 20A) and turn off the cutter motor 230 (although the cutter motor may remain on). With the cutter 216 in its non-deployed position, the screw blade 225 is moved distally toward the cutting edge 250 of the cutter 216. In one example, the lever 241 is moved distally to both drive distal movement of the screw blade 225 and to actuate the conveyor motor 266. As the rotating screw blade 225 is moved distally, the boring bit 239 bores into the collected tissue in the tissue collection chamber 270, and the helical threads 271, 269 on the boring bit and the screw blade 225 pick up the tissue and move the tissue proximally within the tissue-transport passage 223. A stop or plug 224a in the cutter housing 273 restricts movement of the tissue in the tissue collection chamber 270 so that the screw blade 225 can effectively pick up and transport the tissue in the tissue collection chamber. In one embodiment, the stop 224a includes a recess 224b for receiving the distal tip of the boring bit 239 to further facilitate effective pick up of essentially all of the tissue in the tissue collection chamber 270.

Having described embodiments of the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A catheter comprising:
   an elongate catheter body configured to be inserted into a body lumen of a subject, the catheter body having opposite distal and proximal ends, and a body longitudinal axis extending between the distal and proximal ends;
   a cutter located generally at the distal end of the catheter body, the cutter having a proximal end portion, a distal end portion, and a cutter longitudinal axis extending between the proximal and distal end portions, the cutter including a cutting tip at the distal end portion of the cutter and configured to remove tissue from the body lumen;
   a cutter adaptor operatively connected to the cutter to enable rotation of the cutter about the cutter longitudinal axis relative to the cutter adaptor and the catheter body, wherein the cutter adaptor is selectively moveable axially with the cutter relative to the catheter body; and
   a cutter housing adjacent the distal end of the catheter body and defining a cutter window, wherein the cutter housing is selectively pivotable relative to the cutter adaptor between a stowed position, in which the cutting tip of the cutter is received in the cutter housing and non-exposed through the cutter window, and an open position, in which the cutting tip of the cutter is exposed through the cutter window,
   wherein the cutter adaptor and the cutter housing are configured such that (i) proximal movement of the cutter adaptor relative to the catheter body and the cutter housing when the cutter housing is in the stowed position pivots the cutter housing relative to the cutter adaptor toward the open position, and (ii) distal movement of the cutter adaptor relative to the catheter body and the cutter housing when the cutter housing is in the open position pivots the cutter housing relative to the cutter adaptor toward the stowed position.

2. The catheter set forth in claim 1, wherein the cutter adaptor includes a tongue extending distally relative to the cutter, the cutter housing including a closing ramp follower, wherein the closing ramp follower is adapted to run along the tongue as the cutter adaptor is moved distally when the cutter housing is in the open position to pivot the cutter housing relative to the cutter adaptor from the open position toward the stowed position.

3. The catheter set forth in claim 2, wherein the cutter housing defines a tongue slot configured to receive the tongue when the cutter housing is in the closed position to inhibit unintentional pivoting of the cutter housing relative to the cutter adaptor.

4. The catheter set forth in claim 3, wherein the tongue is configured to move axially out of the tongue slot when the cutter adaptor is moved proximally.

5. The catheter set forth in claim 1, wherein at least a portion of the cutting tip is exposed outside the cutter adaptor.

6. The catheter set forth in claim 5, wherein the cutting tip comprises an annular cutting edge.

7. The catheter set forth in claim 6, wherein less than an entire circumference of the annular cutting edge is exposed through the cutter window when the cutter housing is in the open position.

8. The catheter set forth in claim 1, wherein the cutter housing has a housing longitudinal axis extending between proximal and distal ends of the cutter housing, wherein the housing longitudinal axis extends at an offset angle relative to the cutter longitudinal axis when the cutter housing is in the open position.

9. The catheter set forth in claim 8, wherein the offset angle measures from about 5 degrees to about 15 degrees.

10. The catheter set forth in claim 1, wherein the cutter defines a tissue passage extending proximally through the cutter from the cutting tip, wherein the cutter adaptor defines an internal passage in communication with the tissue passage of the cutter for receiving removed tissue passing through the cutter.

11. The catheter set forth in claim 10, wherein the catheter body defines an internal passage extending along the body longitudinal axis, wherein the internal passage defined by the cutter adaptor is in communication with the internal passage defined by the catheter body.

12. The catheter set forth in claim 1, wherein the cutter adaptor includes an adaptor body in which the cutter is received, the cutter housing further comprises an opening ramp follower in the cutter housing, wherein the opening ramp follower is adapted to run along the adaptor body as the cutter adaptor is moved proximally when the cutter housing is in the stowed position to pivot the cutter housing relative to the cutter adaptor from the stowed position to the open position.

13. The catheter set forth in claim 12, wherein the cutter adaptor includes a tongue extending distally relative to the cutter, the cutter housing including a closing ramp follower in the cutter housing, wherein the closing ramp follower is adapted to run along the tongue as the cutter adaptor is moved distally when the cutter housing is in the open position to pivot the cutter housing relative to the cutter adaptor from the open position to the stowed position.

14. The catheter set forth in claim 13, wherein the opening ramp follower and closing ramp follower remain in operative contact with the cutter adaptor in all relative positions of the cutter housing and cutter adaptor.

15. A catheter comprising:
   an elongate catheter body configured for insertion into a body lumen of a subject, the catheter body having opposite distal and proximal ends, and a body longitudinal axis extending between the distal and proximal ends;
   a cutter located generally at the distal end of the catheter body, the cutter having a proximal end portion, a distal end portion, and a cutter longitudinal axis extending between the proximal and distal end portions, the cutter including a cutting tip at the distal end portion of the cutter and configured to remove tissue from the body lumen;
   a cutter adaptor operatively connected to the cutter to enable rotation of the cutter about the cutter longitudinal axis relative to the cutter adaptor and the catheter body, wherein the cutter adaptor is selectively moveable axially with the cutter relative to the catheter body, the cutter adaptor including a tongue extending distally relative to the cutter; and
   a cutter housing adjacent the distal end of the catheter body and defining a cutter window, wherein the cutter housing is selectively pivotable relative to the cutter adaptor between a stowed position, in which the cutting tip of the cutter is received in the cutter housing and non-exposed through the cutter window, and an open position, in which the cutting tip of the cutter is exposed through the cutter window, wherein the cutter housing includes a closing ramp follower adapted to run along the tongue of the cutter adaptor as the cutter adaptor is moved distally to pivot the cutter housing relative to the cutter adaptor from the open position toward the stowed position.

16. The catheter set forth in claim 15, wherein the cutter housing defines a tongue slot configured to receive the tongue when the cutter housing is in the closed position to inhibit pivoting of the cutter housing relative to the cutter adaptor.

17. The catheter set forth in claim 16, wherein the tongue is configured to move axially out of the tongue slot when the cutter adaptor is moved proximally.

18. The catheter set forth in claim 15, wherein at least a portion of the cutting tip is exposed outside the cutter adaptor.

19. The catheter set forth in claim 18, wherein the cutting tip comprises an annular cutting edge.

20. The catheter set forth in claim 15, wherein the cutter adaptor includes an adaptor body in which the cutter is received, the cutter housing further comprising an opening ramp follower, wherein the opening ramp follower is adapted to run along the adaptor body as the cutter adaptor is moved proximally to pivot the cutter housing relative to the cutter adaptor from the stowed position toward the open position.

\* \* \* \* \*